US012704462B2

United States Patent
Boulanger et al.

(10) Patent No.: US 12,704,462 B2
(45) Date of Patent: Aug. 11, 2026

(54) METHOD OF DETECTING THE PRESENCE OF A PATHOGEN IN A BIOLOGICAL LIQUID

(71) Applicant: GREENTROPISM, Paris (FR)

(72) Inventors: Anthony François Michel Claude Dieudonné Boulanger, Paris (FR); Sandrine Castelain, Amiens (FR); Sandrine Godeliève Agnès Lefranc, Montigny-le-bretonneux (FR); Pierre Michel René Gauvain, Saint-Piat (FR); Florent Jules Adrien Perez, Paris (FR); Sanaa El Messaoudi, Sartrouville (FR); Alexandre Antoine Benjamin Marie Banon, Paris (FR); Delphine Stephanie Jeannine Marie-Thérèse Garsuault, Paris (FR); Tiffany Guedet, Nanterre (FR); Marion Schmitt-Boulanger, Paris (FR)

(73) Assignee: SPORE BIOTECHNOLOGIES, Boulogne Billancourt (FR)

( * ) Notice: Subject to any disclaimer, the term of this patent is extended or adjusted under 35 U.S.C. 154(b) by 26 days.

(21) Appl. No.: 17/922,412

(22) PCT Filed: Apr. 30, 2021

(86) PCT No.: PCT/FR2021/050751

§ 371 (c)(1),
(2) Date: Oct. 31, 2022

(87) PCT Pub. No.: WO2021/219969

PCT Pub. Date: Nov. 4, 2021

(65) Prior Publication Data

US 2023/0194432 A1 Jun. 22, 2023

(30) Foreign Application Priority Data

Apr. 30, 2020 (FR) ........................................ 2004334
Oct. 28, 2020 (FR) ........................................ 2011030

(51) Int. Cl.
*G01N 33/553* (2006.01)
*G01N 21/65* (2006.01)
(Continued)

(52) U.S. Cl.
CPC ..... *G01N 21/658* (2013.01); *G01N 33/54346* (2013.01); *G01N 33/553* (2013.01); *G01N 33/56983* (2013.01); *G01N 33/587* (2013.01)

(58) Field of Classification Search
CPC .. G01N 21/658; G01N 33/54346; G06N 3/08; G06N 3/02; G06T 2207/20081
See application file for complete search history.

(56) References Cited

U.S. PATENT DOCUMENTS

2005/0037514 A1* 2/2005 Carron ................ G01N 21/658 436/171

FOREIGN PATENT DOCUMENTS

CN 108872194 A * 11/2018 ............ B82Y 15/00
EP 3901617 A1 10/2021
(Continued)

OTHER PUBLICATIONS

Huayi Shi, "Setting Up a Surface-Enhanced Raman Scattering Database for Artificial-Intelligence-Based Label-Free Discrimination of Tumor Suppressor Genes", 2018 (Year: 2018).*
(Continued)

*Primary Examiner* — Maurice C Smith
(74) *Attorney, Agent, or Firm* — Maier & Maier, PLLC

(57) ABSTRACT

A kit, system and method for the detection of a pathogen, in particular SARS-CoV-2, by surface enhanced Raman spec-
(Continued)

troscopy (SERS) obtained from a sample brought into contact with non-magnetic native metal nanoparticles. The kit includes the non-magnetic native metal nanoparticles and a software designed to detect the presence of the pathogen in the sample.

18 Claims, 8 Drawing Sheets

(51) Int. Cl.
*G01N 33/543* (2006.01)
*G01N 33/569* (2006.01)
*G01N 33/58* (2006.01)

(56) References Cited

FOREIGN PATENT DOCUMENTS

WO WO-2019140305 A1 * 7/2019 .......... A61B 5/0075
WO 2021203041 A1 10/2021

OTHER PUBLICATIONS

Wiley, "Surface-enhanced Raman Spectroscopy (SERS) used in Biosensing Applications", https://analyticalscience.wiley.com/content/news-do/surface-enhanced-raman-spectroscopy-sers-used-biosensing-applications, 2011 (Year: 2011).*
International Search Report issued on Aug. 27, 2021 in corresponding International application No. PCT/FR2021/050751; 5 pages.
Robert Hunter et al. "Optofluidic label-free SERS platform for rapid bacteria detection in serum", Sensors and Actuators B: Chemical, Elsevier BV, NL, vol. 300, Jul. 31, 2019 (Jul. 31, 2019), 9 pgs.
Nawfal Adam Mungroo et al. "SERS based point-of-care detection of food-borne pathogens", Microchim Acta, Springer Verlag, Vienna, AT, vol. 183, No. 2, Dec. 15, 2015 (Dec. 15, 2015), pp. 697-707, 11 pgs.
Elie Akanny et al. "Development of uncoated near-spherical gold nanoparticles for the label-free quantification of Lactobacillus rhamnosus GG by surface-enhanced Raman spectroscopy" Analytical and Bioanalytical Chemistry, Springer Berlin Heidelberg, DE, vol. 411, No. 21, Jun. 17, 2019 (Jun. 17, 2019), pp. 5563-5576, 14 pgs.

* cited by examiner

| Sample | Training score | Test score | Sensitivity | Specificity |
|---|---|---|---|---|
| ARN | 91.1% | 87.5% | 91.7% | 83.3% |
| ARN | 100% | 75% | 75% | 75% |
| ARN | | | 91.7% | 100% |
| ARN | 100% | 80% | 66.7% | 87.3% |
| Inactive | | 87.5% | 100% | 75% |
| Inactive | | 92% | 83% | 100% |
| Inactive | | | 92% | 100% |
| Inactive | | | 100% | 92% |

METHOD OF DETECTING THE PRESENCE OF A PATHOGEN IN A BIOLOGICAL LIQUID

TECHNICAL FIELD

The present invention relates to a kit for detecting the presence of a pathogen by Surface Enhanced Raman Spectroscopy (SERS), the use of said kit and a method for detecting the presence of a pathogen by SERS. This fast and reproducible method has high sensitivity and specificity. The field of the invention is more particularly that of detecting the presence of a pathogen in a biological sample.

BACKGROUND

Various pathogens, including viruses, are responsible for many common human diseases each year, such as upper respiratory infections (rhinitis, pharyngitis), influenza, gastrointestinal infections, or early childhood viral infections such as chickenpox, measles and mumps. Some viral diseases have a significant morbidity or mortality power such as hemorrhagic fevers (EBOLA virus, yellow fever), viral encephalitis (rabies virus, dengue virus, herpes simplex virus, poliovirus), and acquired immunodeficiency syndrome (AIDS). Measles and cytomegalovirus can cause serious abnormalities or death in unborn children. Of the estimated 1,000 to 1,500 types of viruses, about 250 cause disease in humans Several human viruses such as the Epstein Barr virus, papillomaviruses, and hepatitis B and C viruses have also been linked to the development of cancers.

Appearing in China at the end of 2019, the Covid-19 disease is a severe acute respiratory syndrome caused by SARS-CoV-2, a virus belonging to the coronavirus family. The latter, very common, can cause a simple cold or respiratory infection of the lower tract type pneumonia, causing deadly epidemics such as those of severe acute respiratory syndrome (SARS-CoV in 2003), Middle East respiratory syndrome (MERS-CoV in 2012), and now Covid-19 (SARS-CoV-2).

Current Viral Diagnostic Methods Involve:

(i) either the search for the viral particle or one of its components (viral antigens, viral genome or an enzymatic property of a viral protein) and corresponds to direct diagnosis; this search uses rapid detection tests for antigens or molecular biology techniques for the genome (PCR or RT-PCR depending on the nature of the DNA or RNA genome)

(ii) or the search for the host's response to the virus, corresponding to the detection of antibodies specific to the virus sought. This search is mainly done by immunochemistry techniques most often automated such as ELISA ("enzyme-linked-immunosorbent-assay").

The search for the viral genome, which is a sensitive and specific technique widely deployed, requires however heavy and expensive equipment and is often time-consuming.

Currently, for SARS-CoV-2, only a molecular biology test by RT-PCR on a nasopharyngeal swab can confirm a SARS-CoV-2 infection.

Many antigen or serological tests are being deployed and validated. These tests target the Spike surface proteins of the virus or allow to highlight the presence or absence of IgG and/or IgM immunoglobulins depending on the kit.

Raman spectroscopy is a non-invasive chemical analysis method. It is a vibrational spectroscopy like infrared (IR) spectroscopy that provides a simultaneous characterization of the chemical composition of a material, its environment or its degree of oxidation. It is an initially low-sensitivity technique but its low sensitivity has been compensated by the introduction of Surface Enhanced Raman Spectroscopy (SERS). This methodology is based on the use of nanostructured substrates or in the form of metal nanoparticles. The free electrons of the metal oscillate in these nanostructures at the resonance of surface plasmons (Localized Surface Plasmon Resonance, or LSPR), giving rise to a strong localized amplification of the Raman signal of nearby compounds, up to $10^{12}$, allowing to go as far as the detection of single molecules.

To increase the specificity of the technique, it is possible to functionalize the substrate used. These functionalized nanoparticles are intended to bind specifically to biological molecules (such as proteins and nucleic acids) from a pathogen that is being investigated to determine if it is present in the sample. In this case, the presence of peaks in the SERS spectrum obtained from the sample reflects the presence of the pathogen sought. Conversely, molecules that do not come from the pathogen of interest do not see their Raman signal amplified, and contribute only marginally to the SERS signal. In other words, in case of presence of the pathogen in the sample, the SERS spectrometry signal obtained on the basis of said sample includes almost only the contributions of molecules from said pathogen.

In this way, excessive complexity of the SERS spectrum, which would make its interpretation very difficult, is avoided. Indeed, without the functionalization of metal nanoparticles, all the compounds present in the sample are likely to contribute to the Raman spectrum in comparable proportions: this would result in a Raman spectrum whose complexity would make it very difficult to interpret.

However, such a detection process is not entirely satisfactory.

Indeed, because of the functionalization described above, the method of detection of the state of the art is likely to detect only a single pathogen to which the metal nanoparticles are specific, because of their functionalization. The detection of a new pathogen therefore requires the use of different metal nanoparticles, specific to this new pathogen. The result is an inversatile detection process that is tedious to implement.

In addition, the prior art detection process is susceptible to variants and mutations: in other words, it may not detect a variant or mutant of a given pathogen, if the mutation impacts a site where functionalized metal nanoparticles are expected to bind.

Therefore, there is a need to provide a reliable and rapid detection method to detect pathogens, e.g., viruses, including SARS-Cov-2.

SUMMARY

A purpose of the invention is therefore to provide a detection method that is faster, more reproducible, more sensitive and/or more specific than the method of the prior art, while being more versatile (i.e., universal), easier to implement and less sensitive to variants and mutations of pathogens.

The object of the present invention is also to provide:

a computer program product;

a kit for the detection of a pathogen by surface enhanced Raman spectroscopy (SERS); and/or its use for the detection of a pathogen by surface enhanced Raman spectroscopy (SERS) that is likely to solve the problems described above.

The present invention therefore relates to a method for detecting a pathogen in at least one surface enhanced Raman spectroscopy signal obtained from a sample brought into contact with non-magnetic metal nanoparticles, the method being implemented by a computer and comprising:

- a reception of each surface enhanced Raman spectroscopy signal obtained from the sample brought into contact with non-magnetic metal nanoparticles, preferably with non-magnetic native metal nanoparticles;
- an implementation of a classification model configured to associate each surface enhanced Raman spectroscopy signal received with at least one class representative of a presence or absence of the pathogen in the sample.

Indeed, the use of native metal nanoparticles results in a SERS signal that is representative of the presence or absence of any pathogen, without the need for a batch of metal nanoparticles functionalized specifically for a given pathogen.

Although the SERS spectroscopy signal obtained by the method according to the invention is very complex (thus preventing its analysis by an operator), the use of a classification model allows, reliably, to extract from the acquired SERS signal the characteristics to conclude the presence or absence of a given pathogen in the sample.

By "native metal nanoparticle" it is meant, within the meaning of the present invention, a non-functionalized metal nanoparticle, i.e., a naked metal nanoparticle.

According to another aspect, the invention relates to a method for detecting a pathogen in at least one surface enhanced Raman spectroscopy signal, the method comprising:

- a contact of a sample with non-magnetic metal nanoparticles, preferably native;
- an acquisition of at least one surface enhanced Raman spectroscopy signal obtained from the sample brought into contact with the non-magnetic metal nanoparticles;
- a computer's implementation of a classification model configured to associate each acquired surface enhanced Raman spectroscopy signal with at least one class representative of a presence or absence of the pathogen in the sample.

The present invention also relates to a kit for detecting the presence of a pathogen in a sample by surface enhanced Raman spectroscopy (SERS), said kit comprising a lysis buffer (optional), non-magnetic metal nanoparticles (preferably native) and software and/or software medium designed and/or arranged and/or programmed to detect the presence of said pathogen in said sample.

The inventors have shown that non-magnetic metal nanoparticles in suspension can easily and quickly obtain SERS data that is easy to interpret and reproducible.

Very advantageously, in all the examples described, and in all the variants considered, non-magnetic metallic nanoparticles are non-magnetic native metal nanoparticles.

Non-magnetic metal nanoparticles preferably comprise a mixture of metallic non-magnetic nanoparticles of a first metal and non-magnetic nanoparticles of a second metal, the nanoparticles of the first metal being different from the nanoparticles of the second metal. This is advantageous, as nanoparticles made of different metals are likely to amplify Raman scattering photons in different spectral ranges. This results in a richer SERS spectrum, which is likely to facilitate the detection of a desired pathogen.

According to the invention, the lysis buffer, which is optional, may be any buffer known to those skilled in the art capable of solubilizing the proteins of pathogens such as capsid for viruses, membrane proteins or envelope for fungi, yeasts, bacteria or viruses and to release RNA or DNA from the sample. This buffer must be compatible with the SERS technique. Examples include lysis buffers based on Tris (also called tris (hydroxymethyl) aminomethane), EDTA (also called ethylenediaminetetraacetic acid), HEPES (also called 4-(2-hydroxyethyl)-1-piperazine ethane sulfonic acid) or SDS (also called sodium dodecyl sulfate).

According to the invention, the sample may be selected from blood, plasma, saliva, tears, nasopharyngeal fluid, sweat, urine, lymph, cerebrospinal fluid, human or animal tissue or human or animal cells. The sample can also be any liquid such as tap or river water or used to rinse a surface that may be contaminated.

In an advantageous embodiment of the invention, the pathogen which is detected is selected from the group comprising viruses, prions, bacteria, parasites, fungi, yeasts and fragments of all these pathogens. The pathogen is in particular SARS-CoV-2.

Among the viruses that can be detected thanks to the present invention include examples of single-stranded or single-stranded RNA viruses, double-stranded or double-stranded RNA viruses, retroviruses, single-stranded DNA viruses, double-stranded DNA viruses, as defined by the International Committee on Taxonomy of Viruses (ICTV) found at the following link: https://talk.ictvonline.org/ictv-reports/ictv_online_report/

Among the prions that can be detected thanks to the invention include for example transmissible spongiform encephalopathies (TSE) such as the various forms of Creutzfeldt-Jakob disease, fatal familial insomnia (FFI), Gerstmann-Sträussler-Scheinker syndrome (GSSS) and Kuru in humans and animals, scrapie in sheep and goat and bovine spongiform encephalopathy.

Among the parasites that can be detected thanks to the invention include for example parasites of the genus *Plasmodium*, responsible for paludism or malaria, *Sarcocysts*, protozoa such as *Toxoplasma gondii*, responsible for toxoplasmosis.

Among the bacteria that can be detected thanks to the invention include for example, obligate pathogenic bacteria such as *Corynebacterium diphtheriae* agent of diphtheria, *Mycobacterium tuberculosis* which causes tuberculosis, *Mycobacterium leprae* responsible for leprosy; accidental pathogenic bacteria such as *Clostridium tetani* responsible for tetanus and *Vibrio cholerae* which causes cholera; opportunistic pathogenic bacteria such as *Pseudomonas aeruginosa*, or staphylococci of the skin flora.

Among the fungi that can be detected thanks to the invention include, for example, pathogenic fungi causing nosocomial infections such as *Aspergillus fumigatus* responsible for aspergillosis; opportunistic pathogenic fungi such as *Coccidioides immitis* responsible for coccidioidomycosis, *Blastomyces dermatitidis* responsible for blastomycosis, *Histoplasma capsulatum* responsible for histoplasmosis, *Cryptococcus neoformans* or *Cryptococcus gattii* responsible for cryptococcosis; etc.

Among the yeasts that can be detected thanks to the invention include, for example, opportunistic pathogenic yeasts such as those of the *Candida* species such as *Candida albicans* responsible for candidiasis, etc.

In an advantageous embodiment of the invention, the non-magnetic metal nanoparticles have an average diameter between 50 and 200 nm (in particular 50, 60, 70, 80, 90, 100 and/or 200 nm), preferably between 100 and 200 nm (in particular 100, 150 and/or 200 nm), even more advantageously between 100 and 150 nm (in particular 110, 115, 120, 125, 130, 135, 140, 145 and/or 150 nm). Such an average diameter is, for example, measured by surface plasmon resonance (or SPR), transmission electron microscope (TEM), dynamic light scattering (DLS) or Capillary Zone Electrophoresis (CZE).

In another advantageous embodiment of the invention, the non-magnetic metal nanoparticles are nanoparticles of gold, silver, copper, platinum or an alloy based on one of these metals. In the case of mixtures of nanoparticles, the non-magnetic metal nanoparticles of the first metal are preferably gold nanoparticles and the non-magnetic metal nanoparticles of the second metal are preferably silver nanoparticles.

According to the invention the nanoparticles preferably comprise substantially a single metal but may also comprise metal alloys, for example binary alloys.

These nanoparticles are commercially available as solutions or colloidal suspension.

According to the invention in the case of mixtures, the ratio between the two types of nanoparticles is preferably between 5/95 and 95/5 and preferably between 40/60 and 60/40, in particular 50/50. Thus, there can be in the mixture of 5% gold particles and 95% silver nanoparticles expressed by mass relative to the total mass of nanoparticles to 95% gold particles and 5% silver nanoparticles expressed by mass relative to the mass of nanoparticles. In an advantageous embodiment of the invention, the mixture contains 50% by mass of gold nanoparticles and 50% by mass of silver nanoparticles expressed by mass relative to the total mass of nanoparticles.

In the kit according to the invention, the solution or suspension comprising the non-magnetic metal nanoparticles may be in a container which may be for example a test tube with a closure system or a vial with a closure system, or a conical tube with a closure system such as an Eppendorf® type tube.

The present invention also relates to the use of a kit according to the invention comprising non-magnetic metal nanoparticles, and software designed to detect the presence of a pathogen in a sample by surface enhanced Raman spectroscopy (SERS).

Optionally, the software can additionally provide a diagnosis of the disease related to the presence of said pathogen.

This application also relates to a method for detecting the presence of a pathogen in surface enhanced Raman spectroscopy (SERS) data (i.e., based on such data) and/or in a sample that may contain it by surface enhanced Raman spectroscopy (SERS).

According to a first aspect of the detection method according to the invention, said method may comprise:

- reception of surface enhanced Raman spectroscopy (SERS) signals obtained from a sample,
- recognition by a classification model of exalted Raman spectroscopy signals as signals indicating the presence or absence of the pathogen in the sample.

The classification model may include software medium using machine learning or artificial intelligence.

The classification model may include at least one of them: a neural network, a random forest, a support vector machine, a relevance vector machine, a PLSDA, and/or a Bayesian model.

The classification model may include at least one of them: a neural network and/or a random forest.

The method according to the invention may comprise, between reception and recognition, a preprocessing step of surface enhanced Raman spectroscopy signals, preferably comprising at least one of the following pretreatments: a reduction of average, a standard normal variation, normalization by the maximum, a normalization by extrema, a smoothing preferably by Savitzky-Golay algorithm, baseline reduction or correction, order 1 or 2 derivation, principal component analysis (PCA).

The method according to the invention may comprise, between receipt and recognition, a determination of the classification model used among several classification models based on a selection of a form of sample collection and/or a selection of a spectrometer model.

The pathogen that is detected may be selected from the group comprising viruses, prions, parasites, fungi, yeasts, and bacteria and is preferably SARS-CoV-2.

The pathogen may be SARS-CoV-2. In this case, in order to associate each surface enhanced Raman spectroscopy signal received with each class representative of a presence or absence of the pathogen in the sample, the classification model is configured to apply at least one treatment relating to (i.e., taking into account) at least three peaks in the surface exalted Raman spectroscopy signals among:

- a peak at a Raman offset between 419 cm$^{-1}$ and 459 cm$^{-1}$, preferably between 434 cm$^{-1}$ and 444 cm$^{-1}$, or
- a peak at a Raman offset between 566 cm$^{-1}$ and 606 cm$^{-1}$, preferably between 581 cm$^{1}$ and 591 cm$^{1}$, or
- a peak at a Raman offset between 646 cm$^{-1}$ and 686 cm$^{-1}$, preferably between 661 cm$^{1}$ and 671 cm$^{1}$, or
- a peak at a Raman offset between 719 cm$^{-1}$ and 759 cm$^{-1}$, preferably between 734 cm$^{1}$ and 744 cm$^{1}$, or
- a peak at a Raman offset between 839 cm$^{-1}$ and 879 cm$^{-1}$, preferably between 854 cm$^{-1}$ and 864 cm$^{-1}$, or
- a peak at a Raman offset between 962 cm$^{-1}$ and 1002 cm$^{-1}$, preferably between 977 cm$^{-1}$ and 987 cm$^{-1}$, or
- a peak at a Raman offset between 1006 cm$^{-1}$ and 1046 cm$^{-1}$, preferably between 1021 cm$^{-1}$ and 1031 cm$^{-1}$, or
- a peak at a Raman offset between 1121 cm$^{-1}$ and 1161 cm$^{-1}$, preferably between 1136 cm$^{1}$ and 1146 cm$^{1}$, or
- a peak at a Raman offset between 1190 cm$^{-1}$ and 1230 cm$^{-1}$, preferably between 1205 cm$^{-1}$ and 1215 cm$^{-1}$, or
- a peak at a Raman offset between 1339 cm$^{-1}$ and 1379 cm$^{-1}$, preferably between 1354 cm$^{1}$ and 1364 cm$^{1}$, or
- a peak at a Raman offset between 1529 cm$^{-1}$ and 1569 cm$^{-1}$, preferably between 1544 cm$^{-1}$ and 1554 cm$^{-1}$, or
- a peak at a Raman offset between 1591 cm$^{-1}$ and 1631 cm$^{-1}$, preferably between 1606 cm$^{1}$ and 1616 cm$^{1}$, or
- a peak at a Raman offset between 1662 cm$^{-1}$ and 1702 cm$^{-1}$, preferably between 1677 cm$^{-1}$ and 1687 cm$^{-1}$, or
- a peak at a Raman offset between 1722 cm$^{-1}$ and 1762 cm$^{-1}$, preferably between 1737 cm$^{-1}$ and 1747 cm$^{-1}$, or
- a peak at a Raman offset between 1796 cm$^{-1}$ and 1836 cm$^{-1}$, preferably between 1811 cm$^{1}$ and 1821 cm$^{1}$, or
- a peak at a Raman offset between 2058 cm$^{-1}$ and 2098 cm$^{-1}$, preferably between 2073 cm$^{-1}$ and 2083 cm$^{-1}$, or
- a peak at a Raman offset between 2110 cm$^{-1}$ and 2150 cm$^{-1}$, preferably between 2125 cm$^{1}$ and 2135 cm$^{1}$, or
- a peak at a Raman offset between 2322 cm$^{-1}$ and 2362 cm$^{-1}$, preferably between 2337 cm$^{-1}$ and 2347 cm$^{-1}$, or
- a peak at a Raman offset between 2460 cm$^{-1}$ and 2500 cm$^{-1}$, preferably between 2475 cm$^{-1}$ and 2485 cm$^{-1}$.

The pathogen may be SARS-CoV-2. For example, if the sample has been brought into contact with a lysis buffer, in order to associate each surface enhanced Raman spectroscopy signal received with each class representative of a presence or absence of the pathogen in the sample, the classification model is configured to apply at least one treatment relating to (i.e., taking into account) at least three peaks in the surface exalted Raman spectroscopy signals. among:

- a peak at a Raman offset between 456 cm$^{-1}$ and 556 cm$^{-1}$, more preferably between 501 cm$^{1}$ and 511 cm$^{1}$, or

- a peak at a Raman offset between 550 $cm^{-1}$ and 760 $cm^{-1}$, preferably between 560 $cm^{-1}$ and 760 $cm^{-1}$, more preferably between 722 $cm^{-1}$ and 732 $cm^{-1}$, or
- a peak at a Raman offset between 600 $cm^{-1}$ and 970 $cm^{-1}$, preferably between 706 $cm^{-1}$ and 806 $cm^{-1}$, more preferably between 751 $cm^{-1}$ and 761 $cm^{-1}$, or
- a peak at a Raman offset between 750 $cm^{-1}$ and 1160 $cm^{-1}$, preferably between 903 $cm^{-1}$ and 1003 $cm^{-1}$, more preferably between 945 $cm^{-1}$ and 960 $cm^{-1}$, or
- a peak at a Raman offset between 840 $cm^{-1}$ and 1340 $cm^{-1}$, preferably between 964 $cm^{-1}$ and 1064 $cm^{-1}$, more preferably between 1007 $cm^{-1}$ and 1020 $cm^{-1}$, or
- a peak at a Raman offset between 840 $cm^{-1}$ and 1340 $cm^{-1}$, preferably between 1071 $cm^{-1}$ and 1171 $cm^{-1}$, more preferably between 1116 $cm^{-1}$ and 1126 $cm^{-1}$, or
- one peak at a Raman offset between 1000 $cm^{-1}$ and 1380 $cm^{-1}$, preferably between 1104 $cm^{-1}$ and 1204 $cm^{-1}$, more preferably between 1149 $cm^{-1}$ and 1159 $cm^{-1}$, or
- a peak at a Raman offset between 1200 $cm^{-1}$ and 1300 $cm^{-1}$, preferably between 1240 cm-1 and 1270 $cm^{-1}$, more preferably between 1245 $cm^{-1}$ and 1255 $cm^{-1}$, or
- a peak at a Raman offset between 1250 $cm^{-1}$ and 1500 $cm^{-1}$, preferably between 1324 $cm^{-1}$ and 1424 $cm^{-1}$, more preferably between 1368 $cm^{-1}$ and 1380 $cm^{-1}$, or
- a peak at a Raman offset between 1370 $cm^{-1}$ and 1570 $cm^{-1}$, preferably between 1398 $cm^{-1}$ and 1498 $cm^{-1}$, more preferably between 1441 $cm^{-1}$ and 1454 $cm^{-1}$, or
- a peak at a Raman offset between 1440 $cm^{-1}$ and 1710 $cm^{-1}$, preferably between 1509 $cm^{-1}$ and 1609 $cm^{-1}$, more preferably between 1553 $cm^{-1}$ and 1564 $cm^{-1}$, or
- a peak at a Raman offset between 1680 $cm^{-1}$ and 2170 $cm^{-1}$, preferably between 2062 $cm^{-1}$ and 2162 $cm^{-1}$, more preferably between 2107 $cm^{-1}$ and 2117 $cm^{-1}$.

According to a second aspect of the detection method according to the invention, independent but combinable in the first aspect, said method for detecting the presence of a pathogen in a sample that may contain it by surface enhanced Raman spectroscopy (SERS) may comprise:

a) the contact of said sample with non-magnetic metal nanoparticles to obtain a solution or suspension;

b) the deposit of said solution or suspension on a medium; and c) the detection of SERS signals emitted by said deposit.

All steps a) to c) are done at room temperature.

This detection method allows to detect the presence of an infection due to a pathogen and to distinguish in a population between sick individuals (carriers of the pathogen and called positive individuals) and healthy individuals (not carriers of the pathogen and called negative individuals). When the individual has an infection but does not have symptoms of disease then the detection of the presence of the pathogen will be predictive of a risk of developing the disease.

The method according to the invention can be used to evaluate the efficacy of known anti-pathogen drugs or vaccines or to test the efficacy of potential new drugs or anti-pathogen vaccines. A decrease in the amount of the pathogen or an increase in this amount indicates whether therapy is effective or not.

In one embodiment, the sample may be contacted with said non-magnetic metal nanoparticles. In a first embodiment of the method according to the invention is added a sample volume to be tested from about 10 to 200 microliters to about 10 to 2000 microliters of a solution or suspension containing non-magnetic metal nanoparticles or a mixture of non-magnetic nanoparticles of a first metal and non-magnetic nanoparticles of a second metal, The nanoparticles of the first metal are different from the nanoparticles of the second metal. After homogenization by stirring by successive pipetting (no need for vortex), a deposit is made on an aluminum support or a material covered with aluminum foil. The medium can be any type of media commonly used for SERS.

In this embodiment, and optionally, the sample is simultaneously contacted with said non-magnetic metal nanoparticles and with a lysis buffer, before homogenization and deposition described above.

In another embodiment, the sample may be dissolved in a liquid, called "transport medium", before contacting with a centrifugation pellet (also called nanoparticle pellet thereafter) containing said non-magnetic metal nanoparticles.

For example, the sample to be tested is dissolved in the transport medium and then mixed with a nanoparticle pellet obtained by centrifugation of a colloidal suspension of non-magnetic metal nanoparticles as defined above. After homogenization by stirring, a deposit is made on an aluminum support or on a material covered with aluminum foil. The medium can be any type of media commonly used for SERS.

In this embodiment, and optionally, the transport medium is a lysis buffer.

To obtain the pellet of nanoparticles, the suspension of non-magnetic metal nanoparticles as defined above is centrifuged under conditions known to those skilled in the art for example at a centrifugation rate of 700 to 18,000 g during a centrifugation time of between 1 and 50 minutes.

Preferably, to obtain the pellet of nanoparticles, the suspension of non-magnetic metal nanoparticles is centrifuged at a speed of less than 5000 g, preferably less than 2500 g, for example less than or equal to 1000 g. In one example, the suspension of non-magnetic metal nanoparticles centrifuged at a speed equal to 800 g.

This is advantageous as it has been observed that centrifugation at speeds below 5000 g, typically below 1500 g, leads to an increase in the amplitude of the SERS signal. This is likely due to lower mechanical stresses on non-magnetic metal nanoparticles, which would then undergo less deterioration during centrifugation.

Of course, in order to obtain an expected concentration of non-magnetic metal nanoparticles in the centrifugation pellet, the centrifugation time is adapted according to the centrifugation rate. More precisely, for the same centrifuged suspension, and for a given expected concentration of non-magnetic metal nanoparticles in the centrifugation pellet, the centrifugation time generally increases as the centrifugation rate decreases.

For example, a desired concentration of non-magnetic metal nanoparticles in the centrifugation pellet is between 5 g/L and 30 g/L.

In the case where the suspension of non-magnetic metal nanoparticles is centrifuged at a speed of less than 5000 g, preferably less than 2500 g, for example less than or equal to 1000 g, the centrifugation time is, for example, less than one hour.

In an example, the suspension of non-magnetic metal nanoparticles centrifuged at a speed equal to 800 g for 45 min.

According to the invention in the two embodiments described above, the deposit is capable of being dried, under conventional conditions known to those skilled in the art.

Non-magnetic metal nanoparticles may have a diameter between 50 and 200 nm, preferably between 100 and 200 nm, even more preferably between 100 and 150 nm.

Non-magnetic metal nanoparticles of the first metal can be gold particles and non-magnetic metal nanoparticles of the second metal can be silver nanoparticles.

Reception of surface enhanced Raman spectroscopy signals may include:

- an excitation light emission, preferably of wavelength between 750 and 800 nm, said excitation light reaching the sample,
- a capture, by a sensor or spectrometer, of reflected, transmitted, scattered or backscattered light by the sample while said excitation light reaches the sample.

The excitation light can reach the sample and the spectrometer and/or sensor can implement the capture step while the sample has been brought into contact with nanoparticles.

The pathogen that is detected may be selected from the group comprising viruses, prions, parasites, fungi, yeasts and bacteria and is preferably SARS-CoV-2.

According to the invention, any suitable Raman spectrometer system known in the technique and commercially available may be used.

Detection devices, such as optical detectors, radiation sources and computer systems, microprocessors and computer software and algorithms, may be used in any combination to practice the method according to the invention. Accordingly, in some embodiments, software or other computer-readable instructions may be used to interpret, analyze, compile or otherwise analyze output data. The software or other computer system may be used to display, store or transmit output data, whether in digital or other form, to one or more users.

For a given pathogen, the selection of wavelengths is carried out by any technique known to those skilled in the art or described in the literature, in particular through an algorithm as described by Marois M. et al., or by Chen Y. et al., or by Luke G. P. et al.

This method allows to measure the SERS spectra of different pathogens. Each pathogen can be detected because it has a unique SERS spectrum that is significantly different, and therefore distinguishable, from the SERS spectra of other pathogens. Thus, pathogens, especially viruses, have a unique SERS "signature" that distinguishes a biomolecule of interest or a combination of particular biomolecules from other biomolecules or base media.

Typically, in the presence of an inactivated pathogen or in the absence of a pathogen, a first surface exalted Raman spectroscopic signature is obtained and when the pathogen is present a second exalted Raman spectroscopic signature of different surface from the first.

The invention also relates to software medium, designed and/or arranged and/or programmed to implement a method according to the invention (preferably the first aspect of the method according to the invention).

The invention also relates to a system, designed and/or arranged and/or programmed to implement a method according to the invention (preferably the first and/or second aspect of the method according to the invention).

The inventors found that the presence of SARS-CoV-2 in a sample for gold nanoparticles is characterized by the presence of a peak between 560 $cm^{-1}$ and 760 $cm^{-1}$ (typically at 660 or 727 $cm^{-1}$, preferably 660 $cm^{-1}$), a peak between 1250 and 1500 $cm^{-1}$ (typically at 1374 $cm^{-1}$) and a peak between 2062 $cm^{-1}$ and 2162 $cm^{-1}$ (typically at 2100 or 2112 $cm^{-1}$, preferably 2100 $cm^{-1}$). The patient from whom the sample was taken is said to be positive for SARS-CoV-2. On the other hand, in the absence of virus in a sample, only a peak between 1100 and 1250 nm is visible. The patient is then declared negative for SARS-CoV-2.

The invention also relates to the use of a kit according to the present invention wherein the software further provides a diagnosis of the disease related to the presence of said pathogen.

BRIEF DESCRIPTION OF THE FIGURES

Other advantages and features of the invention will appear upon reading the detailed description of implementations and embodiments in no way limiting, and the following accompanying drawings.

DETAILED DESCRIPTION

Figures 1, 2:
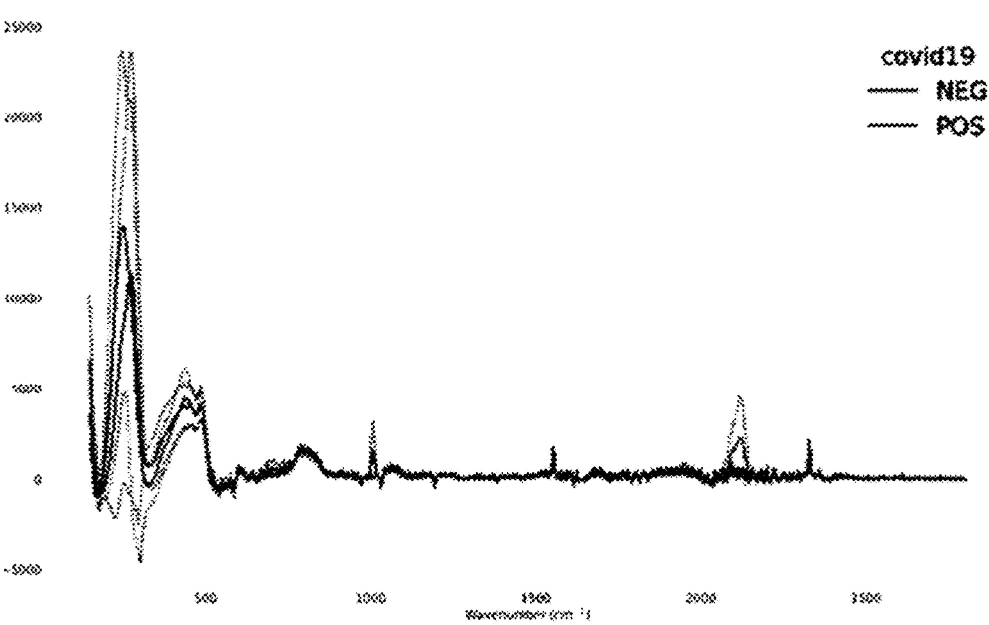
FIG. 1 illustrates the results obtained with nasopharyngeal swabs from 20 different people with 3 samples for each sample. The experimental conditions are those of Example 1 of the invention FIG. 2 gives the spectra obtained under the conditions of Example 1 for positive patients in whom the presence of Covid-19 was detected (in black) and in negative patients in whom the presence of Covid-19 was not detected (in gray)

On all the spectra of FIGS. 2, 3, 5, 6, 9 and 10:

the abscissa is the Raman shift in $cm^{-1}$, and the ordinate is an intensity in arbitrary units.

These embodiments are in no way limiting, one may consider in particular variants of the invention comprising only a selection of features described or illustrated subsequently isolated from the other features described or illustrated (even if this selection is isolated within a sentence comprising these other characteristics), if this selection of features is sufficient to confer a technical advantage or to differentiate the invention from prior art. This selection includes at least one functional preference feature without structural details, and/or with only part of the structural details if this part alone is sufficient to confer a technical advantage or to differentiate the invention from the prior art.

In a first embodiment not limiting, a kit according to the invention for detecting the presence of a pathogen in a sample by surface enhanced Raman spectroscopy (SERS) comprises non-magnetic metal nanoparticles and software and/or software medium designed and/or arranged and/or programmed to detect the presence of said pathogen in said sample.

Very advantageously, in all the examples described, and in all the variants considered, non-magnetic metallic nanoparticles are non-magnetic native metal nanoparticles.

Optionally, the kit according to the invention also comprises a lysis buffer.

The technical functions of this software or these software media will be described in more detail below.

The pathogen that is detected is selected from the group comprising viruses, prions, parasites, fungi, yeasts and bacteria and is in particular SARS-CoV-2.

Preferably, the non-magnetic metal nanoparticles have an average diameter between 50 and 200 nm, preferably between 100 and 200 nm, even more preferably between 100 and 150 nm.

Preferably, non-magnetic metal nanoparticles are particles of gold, silver, copper, platinum or an alloy based on one of these metals. In particular, gold, silver and/or platinum are used because these metals do not alter biological samples.

For example, non-magnetic metal nanoparticles comprise a mixture of non-magnetic nanoparticles of a first metal and non-magnetic nanoparticles of a second metal, the nanoparticles of the first metal being different from the nanoparticles of the second metal.

In this case, and preferably, the non-magnetic metal nanoparticles of the first metal are gold nanoparticles and the non-magnetic metal nanoparticles of the second metal are silver nanoparticles.

This kit includes non-magnetic metal nanoparticles and software designed to detect the presence of a pathogen in a sample by surface enhanced Raman spectroscopy (SERS). As mentioned above, the kit optionally includes a lysis buffer.

The software or software medium of the kit may also, but optionally, provide a diagnosis of the disease related to the presence of said pathogen.

Figure 4:
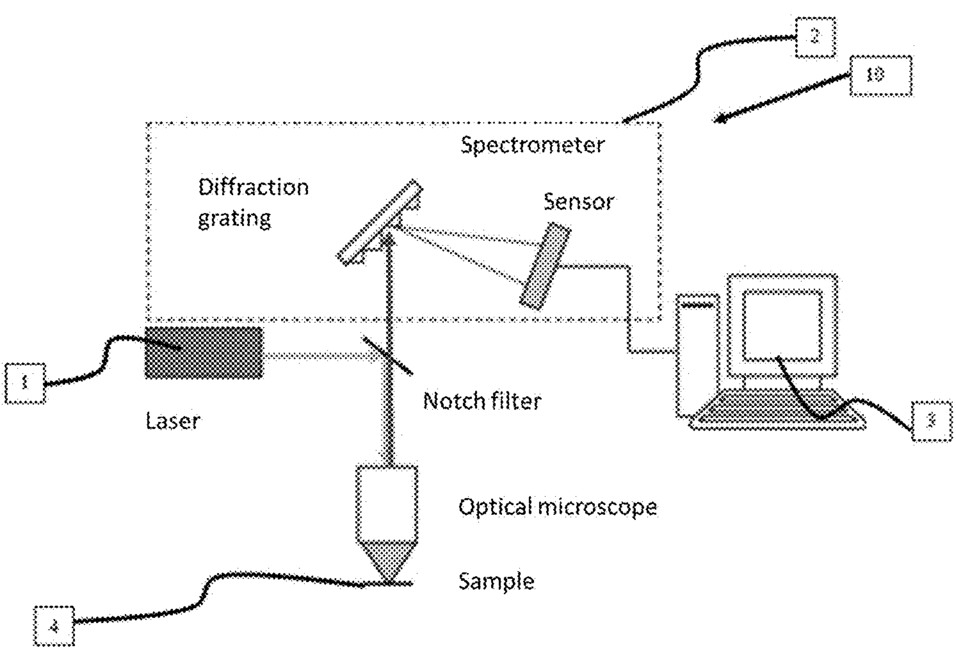
FIG. 4 is a schematic view of a first embodiment of system 10 according to the invention

A first embodiment of system 10 according to the invention comprises:

- an optical device as shown in FIG. 4, comprising:
  - a sample holder 4,
  - a source 1 (typically a laser) for emission of excitation light, said light comprising at least a wavelength between 750 and 800 nm (for example a wavelength at 785 nm), said source 1 being arranged so that said excitation light reaches a sample on the sample holder,
  - a sensor or spectrometer 2 (typically a Raman spectrophotometer), and arranged to capture reflected, transmitted, scattered or backscattered light by the sample while said excitation light reaches the sample; element 2 typically comprises a diffraction grating arranged to diffract reflected, transmitted, scattered or backscattered light by the sample and a detector arranged to detect the light so diffracted,
- the software or software medium of the kit,
- an analysis unit 3, comprising at least one computer, a central or computing unit, an analog electronic circuit (preferably dedicated), a digital electronic circuit (preferably dedicated), and/or a microprocessor (preferably dedicated), and arranged and/or programmed to implement the software or software medium of the kit.

In the case where the source 1 is a laser, said source 1 is, for example, configured to deliver a laser beam having a power between 100 mW and 1 W, for example 500 mW. In the latter case, the deposit is illuminated for a few seconds, typically between 0.1 s and 20 s, for example between 1 s and 7 s.

The first embodiment of method of using the kit and/or detecting a pathogen in surface enhanced Raman spectroscopy (SERS) data, implemented in system 10, will now be described.

In this first embodiment of method according to the invention, the unit 3 receives surface enhanced Raman spectroscopy signals generated as follows:

a) a sample (typically a biological specimen such as preferably a salivary or nasopharyngeal sample from a man or animal) is contacted with non-magnetic metal nanoparticles to obtain a solution or suspension; then b) said solution or suspension is deposited on a support, more precisely on the sample holder 4 and c) SERS signals emitted by said pathogen are detected, the signals indicating the presence of said pathogen, preferably by:
   - an emission (by source 1) of excitation light, preferably of wavelength between 750 and 800 nm, said excitation light reaching the sample; said excitation light reaches the sample while the sample is in contact with the nanoparticles,
   - a capture, by the sensor or spectrometer 2, of reflected, transmitted, scattered or backscattered light by the sample while said excitation light reaches the sample; The spectrometer or sensor 2 implements the capture step while the sample is in contact with the nanoparticles.

As previously stated, non-magnetic metal nanoparticles include, for example, a mixture of non-magnetic nanoparticles of a first metal and non-magnetic nanoparticles of a second metal, the nanoparticles of the first metal being different from the nanoparticles of the second metal. In this case, the non-magnetic metal nanoparticles of the first metal are, for example, gold particles and the non-magnetic metallic nanoparticles of the second metal are, for example, silver nanoparticles.

Preferably, the non-magnetic metal nanoparticles have a diameter between 50 and 200 nm, preferably between 100 and 200 nm, even more preferably between 100 and 150 nm.

Depending on the variant considered:

- the sample is dissolved in a transport medium before contacting with a centrifugation pellet containing the said non-magnetic metal nanoparticles, or
- the sample is simultaneously brought into contact with said non-magnetic metal nanoparticles.

In each variant, the non-magnetic metal nanoparticles are, in particular in colloidal suspension, for example in sodium citrate.

Alternately:

- the sample is dissolved in lysis buffer before contact with the centrifugation pellet, or
- the sample is simultaneously brought into contact with a lysis buffer and with non-magnetic metal nanoparticles.

Then, the unit 3 performs the following steps:

- a receipt by the unit 3 of surface enhanced Raman spectroscopy (SERS) signals from sensor 2 or spectrometer 2 and obtained from the sample, recognition, by a classification model (part of the software or software medium of the kit), of exalted Raman spectroscopy signals as signals indicating the presence or absence of the pathogen in the sample.

In this description, the terms "surface enhanced Raman spectroscopy (SERS) signals" or "surface enhanced Raman spectroscopy (SERS) data" will be used interchangeably.

Surface enhanced Raman spectroscopy (SERS) signals comprise Raman shift data between at least 1000 $cm^{-1}$ and 1500 $cm^{-1}$, preferably at least between 750 $cm^{-1}$ and 2000 $cm^{-1}$, even more preferably at least between 500 $cm^{-1}$ and 2300 $cm^{-1}$.

The spectrometer 2 is for example:

- an STRam spectrometer providing Raman offset data between 499.46 and 2801.89 $cm^{-1}$; or
- a MIRA spectrometer providing Raman shift data between 499 and 2300 $cm^{-1}$.

The classification model includes the software medium of the kit which are software medium by machine learning (or artificial intelligence) or artificial intelligence.

The classification model includes at least one of them: a neural network, a random forest, a support vector machine, a relevance vector machine, a PLS-DA (Partial least squares discriminant analysis), and/or a Bayesian model. Preferably, the classification model includes at least one of: a neural network and/or a random forest.

Optionally, the method comprises, between reception and recognition, a step of preprocessing the signals of exalted Raman spectroscopy, preferably comprising at least one of the following pretreatments: a reduction of average, a standard normal variation (SNV), normalization by the maximum, normalization by extrema, a smoothing preferably by Savitzky-Golay algorithm, a reduction or correction of baseline, a preference derivation of order 2, a Principal Component Analysis (PCA).

The method includes, between receipt and recognition, a determination of the classification model used among several predetermined classification models based on:

- a form of sample collection (typically, a user enters on a keyboard or touch screen of the unit 3 the form of the sample tested, typically nasopharyngeal or saliva); and/or
- a spectrometer model 2 (typically, a default choice is programmed and/or a user enters on a keyboard or touch screen of the unit 3 the spectrometer model 2 (typically STRam or MIRA) used in system 10); and/or
- a sample transport medium; and/or
- data relating to the subject from which the sample was taken, such as symptomatology, results of additional examinations (e.g. medical imaging results), age, sex; and/or
- the pathogen(s) to be detected.

Such a choice is preferably made automatically.

The pathogen sought to be detected is one of the elements of the group including viruses, prions, parasites, fungi, yeasts and bacteria and is preferably SARS-CoV-2 (severe acute respiratory syndrome coronavirus 2).

In this case, in order to associate each surface enhanced Raman spectroscopy signal received with each class representative of a presence or absence of the pathogen in the sample, the classification model is configured to apply at least one treatment relating to (i.e. taking into account) at least three peaks in the surface exalted Raman spectroscopy signals among:

- a peak at a Raman offset between 419 $cm^{-1}$ and 459 $cm^{-1}$, preferably between 434 $cm^{-1}$ and 444 $cm^{-1}$, or
- a peak at a Raman offset between 566 $cm^{-1}$ and 606 $cm^{-1}$, preferably between 581 $cm^{-1}$ and 591 $cm^{-1}$, or
- a peak at a Raman offset between 646 $cm^{-1}$ and 686 $cm^{-1}$, preferably between 661 $cm^{-1}$ and 671 $cm^{-1}$, or
- a peak at a Raman offset between 719 $cm^{-1}$ and 759 $cm^{-1}$, preferably between 734 $cm^{-1}$ and 744 $cm^{-1}$, or
- a peak at a Raman offset between 839 $cm^{-1}$ and 879 $cm^{-1}$, preferably between 854 $cm^{-1}$ and 864 $cm^{-1}$, or
- a peak at a Raman offset between 962 $cm^{-1}$ and 1002 $cm^{-1}$, preferably between 977 $cm^{-1}$ and 987 $cm^{-1}$, or
- a peak at a Raman offset between 1006 $cm^{-1}$ and 1046 $cm^{-1}$, preferably between 1021 $cm^{-1}$ and 1031 $cm^{-1}$, or
- a peak at a Raman offset between 1121 $cm^{-1}$ and 1161 $cm^{-1}$, preferably between 1136 $cm^{1}$ and 1146 $cm^{1}$, or
- a peak at a Raman offset between 1190 $cm^{-1}$ and 1230 $cm^{-1}$, preferably between 1205 $cm^{-1}$ and 1215 $cm^{-1}$, or
- a peak at a Raman offset between 1339 $cm^{-1}$ and 1379 $cm^{-1}$, preferably between 1354 $cm^{1}$ and 1364 $cm^{1}$, or
- a peak at a Raman offset between 1529 $cm^{-1}$ and 1569 $cm^{-1}$, preferably between 1544 $cm^{-1}$ and 1554 $cm^{-1}$, or
- a peak at a Raman offset between 1591 $cm^{-1}$ and 1631 $cm^{-1}$, preferably between 1606 $cm^{1}$ and 1616 $cm^{1}$, or
- a peak at a Raman offset between 1662 $cm^{-1}$ and 1702 $cm^{-1}$, preferably between 1677 $cm^{-1}$ and 1687 $cm^{-1}$, or
- a peak at a Raman offset between 1722 $cm^{-1}$ and 1762 $cm^{-1}$, preferably between 1737 $cm^{-1}$ and 1747 $cm^{-1}$, or
- a peak at a Raman offset between 1796 $cm^{-1}$ and 1836 $cm^{-1}$, preferably between 1811 $cm^{1}$ and 1821 $cm^{1}$, or
- a peak at a Raman offset between 2058 $cm^{-1}$ and 2098 $cm^{-1}$, preferably between 2073 $cm^{-1}$ and 2083 $cm^{-1}$, or
- a peak at a Raman offset between 2110 $cm^{-1}$ and 2150 $cm^{-1}$, preferably between 2125 $cm^{1}$ and 2135 $cm^{1}$, or
- a peak at a Raman offset between 2322 $cm^{-1}$ and 2362 $cm^{-1}$, preferably between 2337 $cm^{-1}$ and 2347 $cm^{-1}$, or
- a peak at a Raman offset between 2460 $cm^{-1}$ and 2500 $cm^{-1}$, preferably between 2475 $cm^{-1}$ and 2485 $cm^{-1}$.

Indeed, the inventors found that peaks at 439, 586, 666, 739, 859, 982, 1026, 1141, 1210, 1359, 1549, 1611, 1682, 1742, 1816, 2078, 2130, 2342 and/or 2480 $cm^{-1}$ were particularly discriminating for the detection of SARS-CoV-2 in a sample.

If the pathogen is SARS-CoV-2 and the sample is placed in the presence of lysis buffer, in order to associate each surface enhanced Raman spectroscopy signal received with each class representative of a presence or absence of the pathogen in the sample, the classification model is configured to apply at least one treatment relating to (i.e. taking into account) at least three peaks (preferably at least five peaks, more preferentially at least eight peaks) in the signals of Raman spectroscopy exalted among:

- a peak (101) at a Raman offset between 456 $cm^{-1}$ and 556 $cm^{-1}$, more preferably between 501 $cm^{-1}$ and 511 $cm^{-1}$, or
- a peak (102) at a Raman offset between 550 $cm^{-1}$ and 760 $cm^{-1}$, preferably between 560 $cm^{-1}$ and 760 $cm^{-1}$, more preferably between 722 $cm^{-1}$ and 732 $cm^{-1}$, or
- a peak (103) at a Raman offset between 600 $cm^{-1}$ and 970 $cm^{-1}$, preferably between 706 $cm^{-1}$ and 806 $cm^{-1}$, more preferably between 751 $cm^{-1}$ and 761 $cm^{-1}$, or
- a peak (104) at a Raman offset between 750 $cm^{-1}$ and 1160 $cm^{-1}$, preferably between 903 $cm^{-1}$ and 1003 $cm^{-1}$, more preferably between 945 $cm^{-1}$ and 960 $cm^{-1}$, or
- a peak (105) at a Raman offset between 840 $cm^{-1}$ and 1340 $cm^{-1}$, preferably between 964 $cm^{-1}$ and 1064 $cm^{-1}$, more preferably between 1007 $cm^{-1}$ and 1020 $cm^{-1}$, or a peak (106) at a Raman offset between 840 $cm^{-1}$ and 1340 $cm^{-1}$, preferably between 1071 $cm^{-1}$ and 1171 $cm^{-1}$, more preferably between 1116 $cm^{-1}$ and 1126 $cm^{-1}$, or one (107) peak at a Raman offset between 1000 $cm^{-1}$ and 1380 $cm^{-1}$, preferably between 1104 $cm^{-1}$ and 1204 $cm^{-1}$, more preferably between 1149 $cm^{-1}$ and 1159 $cm^{-1}$, or a peak at a Raman offset between 1200 $cm^{-1}$ and 1300 $cm^{-1}$, preferably between 1240 $cm^{-1}$ and 1270 $cm^{-1}$, more preferably between 1245 $cm^{-1}$ and 1255 $cm^{-1}$, or a peak (109) at a Raman offset between 1250 $cm^{-1}$ and 1500 $cm^{-1}$, preferably between 1324 $cm^{-1}$ and 1424 $cm^{-1}$, more preferably between 1368 $cm^{-1}$ and 1380 $cm^{1}$, or a peak (110) at a Raman offset between 1370 $cm^{-1}$ and 1570 $cm^{-1}$, preferably between 1398 $cm^{-1}$ and 1498 $cm^{-1}$, more preferably between 1441 $cm^{-1}$ and 1454 $cm^{-1}$, or a peak (111) at a Raman offset between 1440 $cm^{-1}$ and 1710 $cm^{-1}$, preferably between 1509 $cm^{-1}$ and 1609 $cm^{-1}$, more preferably between 1553 $cm^{-1}$ and 1564 $cm^{-1}$, or a peak (112) at a Raman offset between 1680 $cm^{-1}$ and 2170 $cm^{-1}$, preferably between 2062 $cm^{-1}$ and 2162 $cm^{-1}$, more preferably between 2107 $cm^{-1}$ and 2117 $cm^{-1}$.

Database

Machine learning, through the classification model, was built on a database.

For example, for the classification model specific to the form of nasopharyngeal swab, the database consists of 110 specimens (i.e. patients): 55 nasopharyngeal swabs from COVID-19 positive (POS) patients and 55 nasopharyngeal swabs from COVID-19 negative (NEG) patients. The SARS-CoV-2 virus screening test was performed using the RT-PCR (Reverse Transcription-Polymerase Chain Reaction) method. The samples and tests were carried out at the University Hospital of Amiens.

Each sample was prepared with nanoparticles as previously described. This preparation is then placed on three separate slides (later called deposits). Each deposit is analyzed three times by Raman spectroscopy in System 10 resulting in a total of 9 spectra per sample. A set of spectra relating to a patient is called a series. In addition, 8 positive and 8 negative patients were repeatedly measured on another day of analysis to control a possible impact of the experimental conditions on the Raman measurement. These data were included in the database, resulting in a total of 567 spectra labeled “POS” and 567 spectra labeled “NEG”.

Figure 5:
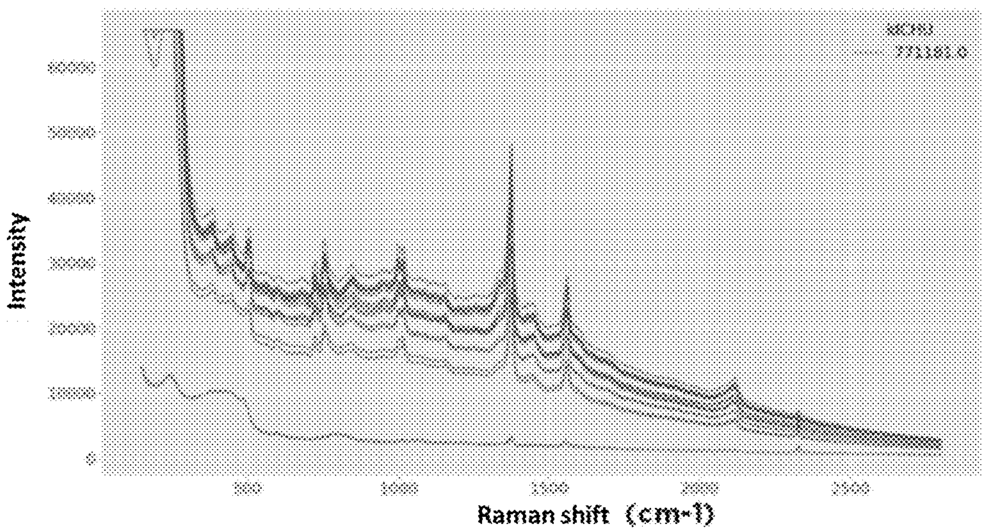
FIG. 5 shows a series of measurements (surface enhanced Raman spectroscopy (SERS) signals) performed with the STRam spectrometer for a patient

Since these are data from a laboratory protocol, it is possible that experimental factors have an impact on the spectra (e.g. preparation or deposition poorly performed, spectral analysis on the edge of the deposit, poor reference of the spectrometer . . . ). These hazards can generate a spectral pace different from that expected, in which case we will speak of “outlier” spectrum, i.e., “aberrant” spectra. Several methods can be used to work with these spectra: they should first be identified and then discarded. We can then choose to train a model only on non-outliers spectra or to integrate them into the database in order to train a predictive model to identify them (we can then imagine a software alert specifying that a measurement is improperly performed and that it will not be taken into account). Since the final result is accompanied by a probability of belonging to the class directly influenced by the shape of the spectrum, the outliers are removed from the database. FIG. 5 shows a series of measurements made with the STRam spectrometer for a patient 771181 where outliers spectra are present.

On these spectra, there are two phenomena. First, two spectra look radically different from the rest of the measurement series. These are two spectra with a low intensity and therefore reflecting an acquisition not properly targeting the deposit made on the slide. These two spectra have therefore been removed from the database. Secondly, there is a phenomenon of signal saturation at the beginning of the range. This phenomenon, occurring on a large part of the database, has created a particular choice for the pre-treatments described below.

The example of FIG. 5 presents a particular case of outliers for a particular sample (patient 771181), the analysis carried out on the 110 patients resulted in a consequent filtering of the database detailed in Table 1, which illustrates the number of spectra present in the base after filtering for STRam and MIRA spectrometers.

TABLE 1

| Spectrometer | Label | Initial number of spectra | Final number of spectra |
|---|---|---|---|
| STRam | POSITIVE (POS) | 567 | 447 |
| | NEGATIVE (NEG) | 567 | 504 |
| MIRA | POSITIVE (POS) | 567 | 516 |
| | NEGATIVE (NEG) | 567 | 507 |

These filtered databases are those that served as training and validation games for the predictive classification models of the unit 3 described in the next part.

Figure 15:
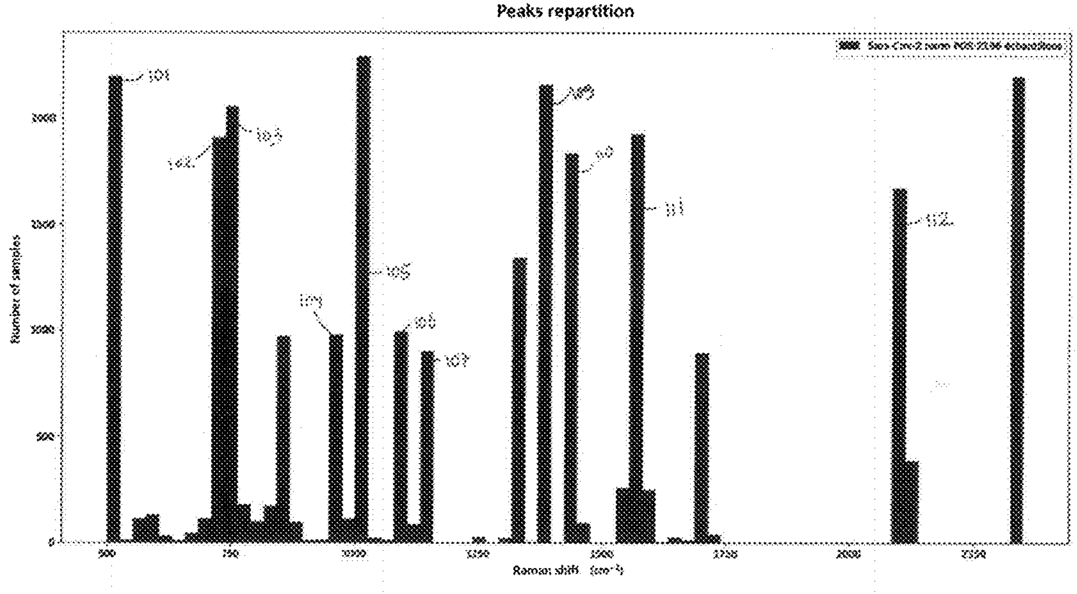
FIG. 15 illustrates the distribution of Raman shift peaks for 2196 SARS-Cov-2 positive samples.

FIG. 15 illustrates the distribution of Raman offset peaks for 2196 SARS-Cov-2 positive samples. Peaks 101 to 107 and 109 to 112, whose presence is indicative of the presence of SARS-CoV-2, are visible in FIG. 15.

Classification Models of the Unit 3

When working with a binary classifier, the basic tool for analyzing prediction performance is the confusion matrix. This is a 2×2 double-entry table comparing predicted labels with actual labels, as shown in Table 2.

TABLE 2

| | | | |
|---|---|---|---|
| Real label | NEG | TN | FP |
| | POS | FN | TP |
| | | NEG | POS |
| | | Predicted label | |

This type of matrix directly highlights the strengths and weaknesses of the classifier. Indeed, we seek to maximize the number of true negatives (TN) and true positives (TP), which correspond to correct predictions, while minimizing the number of false negatives (FN) and false positives (FP), which correspond to errors. We can also calculate metrics directly from these quantities:

$$\text{Precision} = \frac{VP + VN}{VP + FP + VN + FN}$$

$$\text{Sensitivity} = \frac{VP}{VP + FN}$$

$$\text{Specificity} = \frac{VN}{VN + FP}$$

These three metrics are important quantities when trying to quantify the performance of a binary classifier. Accuracy is the percentage of correctly predicted items. Sensitivity is the probability that the classifier will return "POS" if the disease is actually present. Similarly, specificity is the probability that the classifier will return "NEG" for a non-ill patient. When working with a binary classifier, a precision, sensitivity or specificity value close to 0.5 means that one makes as good a prediction as a random choice while approaching 1.0 shows good predictive power.

Maximizing accuracy is necessarily a good thing. Indeed, the closer it is to 1.0, the higher the percentage of correctly classified spectra. However, a disease screening test will often limit itself to maximizing the specificity of the model (while maintaining the highest possible sensitivity). Indeed, we prefer to be sure that a test declaring "NEG" is not wrong while we can confirm a test declaring "POS" by repeating the test for example. In the context of a pandemic, such as SARS-CoV-2, the approach must be different. Indeed, it is crucial to properly detect if a patient has the disease in order to prevent it from infecting others and declaring a patient as positive if he is not can be considered an acceptable risk. With this in mind, the choice of the best models is mainly based on the criterion of sensitivity.

Optimizing predictive models is computationally resource-intensive, both dependent on the number and size of data. Since it is necessary to compare the performance of several models, which must be optimized beforehand, reducing the size of the data is a pre-processing that can greatly improve computation times. For this reason, the data from the MIRA 2 spectrometer and STRam were transformed by Principal Component Analysis (PCA). This method diagonalizes the covariance matrix of a dataset to extract the eigenvectors. These vectors, also called principal components, then serve as a new basis on which to project the data. PCA greatly reduces the size of the data while retaining the relevant part of the information present in the initial set. For example, the 951 spectra coming out of the STRam have 1959 points but an ACP allows, by using 12 components, to retain more than 99.9% of the internal variability of the data. We then go from a matrix of size 951×1959 to a matrix of size 951×12 while keeping almost all the information. Some models, sensitive to the dimensionality of the data, are optimized in a time 100 times less by doing so.

Figure 6:
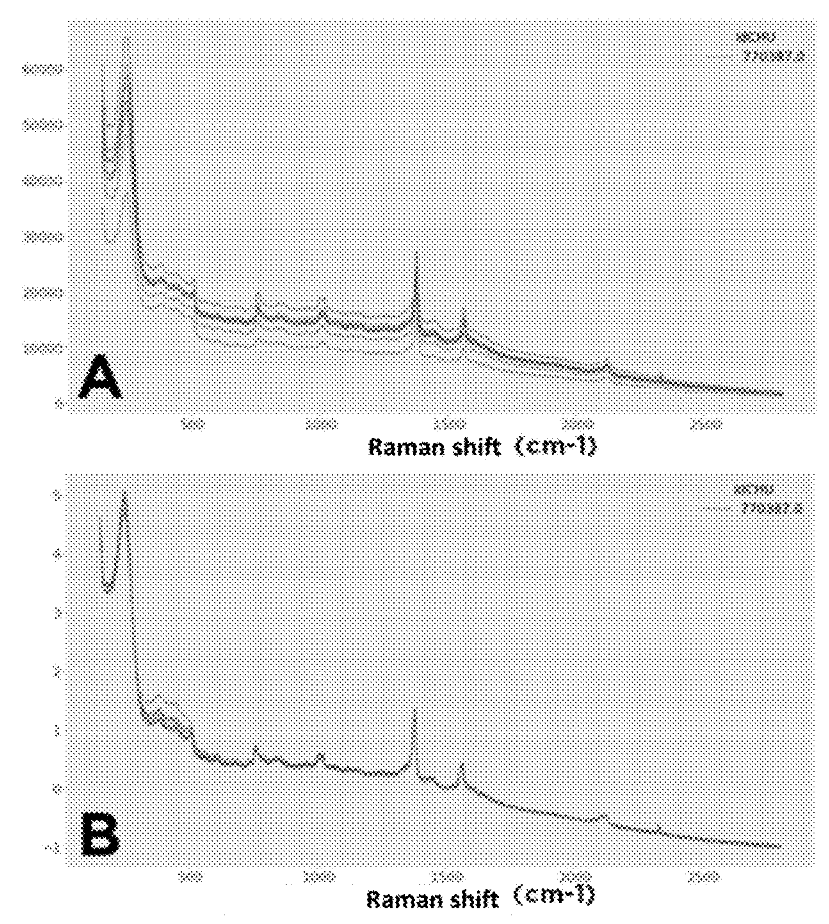
FIG. 6 shows a series of measurements (surface enhanced Raman spectroscopy (SERS) signals) before and after pretreatment with SNV (Measurement series before (A) and after (B) pretreatment with SNV, data measured by STRam spectrometer)

Before reducing the size of the data, the spectra were preprocessed by SNV (Standard Normal Variate). This is a common pre-treatment in the chemometric community that consists of subtracting from each spectrum its mean (centering) and dividing it by its standard deviation. After pre-treatment with SNV, a spectrum has a zero mean and a unit standard deviation. FIG. 6 shows a series of measurements before and after pre-treatment with SNV (Measurement series before (A) and after (B) pretreatment with SNV, data measured by STRam). Such pre-treatment is optional.

The intensity acquired for spectra depends on the optical path taken by the light during the measurement, which in turn depends on the nature of the sample. Thus, depending on the matrix that is scanned it can be difficult to have perfectly reproducible measurement conditions. The SNV allows to reduce very strongly the variations in the general intensity of the spectra and to tighten the measurement series, as can be seen between the spectra of panel A and panel B of FIG. 6.

There is a wide variety of classification models. Within the framework of the embodiments of the present invention, several classifiers programmed in Python have been trained: neural networks, random forests, support vector machines, relevance vector machines, PLSDA and Bayesian models.

In order to measure the performance of the different models, the principle of cross-validation (CV) is used. This method divides the training database into K parts (or "groups"), which is called K-fold cross-validation. In the embodiments described herein, we have chosen K=10. Each of the 10 parts of the database contains substantially the same distribution of positive and negative spectra as the original database, so this is referred to as stratified cross-validation. In addition, these groups are not randomly cut. Indeed, the 9 spectra of a patient are necessarily present in the same group in order to avoid any bias in performance Once the database is divided into 10 parts, a model is successively trained on 9 of them and tested on the last one. Finally, the model is trained 10 times and tested on all the different pieces of the base, i.e. the different parts of the base. By using the 10 model performances obtained, i.e. the model performance on each of the 10 parts of the database, we obtain the performance of the model in cross-validation. In this case, for each model, the corresponding performance is the accuracy (defined above) obtained by means of that model.

In machine learning, we speak of hyper-parameter when a parameter of a model is adjusted by the user and not during training. The other parameters are called "predictive parameters".

Almost all models have hyper-parameters. For example, a classifier based on random forests has up to 17. Some are less interesting than others but it is necessary to correctly adjust these hyper-parameters to obtain the best possible modeling. With this in mind, the hyper-parameters of all the models that were tested were selected using an exhaustive analysis, called "GridSearch". This approach uses an estimator (e.g. a random forest) and a hyperparameter space that needs to be tested. All possible combinations in the space of the hyperparameters provided are then tested and are associated with a cross-validation score.

When a model has a large number of hyper-parameters that we seek to optimize, the GridSearch can quickly generate a large number of estimators (i.e. predictive parameters) to optimize. Indeed, when models have a large number of hyperparameters, it is possible that the optimal parameters differ from one hyperparameter space to another. In this case, all hyperparameter spaces are tested, and models are constructed with all possible combinations of parameters; Finally, the model with the highest performance (and therefore the predictive parameters and hyper-parameters associated with this model) is retained.

Table 3 presents one of the hyperparameter spaces that can be considered for a random forest (these parameters will be detailed in more detail later):

TABLE 3

| | |
|---|---|
| Number of estimators (i.e. the number of trees present in the forest) "N estimators" | 100, 200, 350, 500, 800 |
| Maximum number of characteristics (i.e. the number of characteristics (here, Raman offsets) to be taken into account when judging the quality of a node of the tree. For example, if we choose, square root, this value will be the square root of the total number of Raman offsets in the data.) "Max. features" | Auto, square root (sqrt), log2 |
| Maximum depth (i.e. the number of "floors" of the tree. If it is set to 10, then the final leaves of the tree will be reached after 10 nodes) | 2, 3, 4, 5, 6, 7, 8, 9, 10, 11, 12, 13, 14, 15 |

TABLE 3-continued

| | |
|---|---|
| "Max. depth" | |
| Criterion (i.e. the criterion used to judge the quality of a node) "Criterion" | Shannon entropy, Coeff. Gini |
| Bootstrap (This is a method of randomizing the training database to train all trees in the forest on slightly different data) | Yes, No |

Such a hyperparameter space generates 840 different combinations of parameters. In addition, each model is trained in K-fold cross-validation with K=10, which makes a total of 8400 models to train and can represent several hours of calculation. We can then select the highest cross-validation score among the 8400 calculated scores and thus find the most optimized parameterization.

For each type of model we then have the best parameterization and an associated cross-validation score. It is then possible to select the model giving the best results on the STRam data and the MIRASA data (the MIRASA data being the data obtained by means of a MIRA spectrometer). The best modeling obtained for STRam data is a random forest, the one obtained for MIRASA data is a neural network (multi-layer Perceptron).

Random Forest

Before describing how a random forest works, it is important to understand what a decision tree is. Decision trees are predictive models that can be used in both classification and regression. This is the first of these cases that interests us here.

A decision tree corresponds to a flowchart that will test the values of the different predictive parameters and advance in the graph according to the tests it performs.

The training of such a model consists in finding, from the data and labels of the training base (i.e. the real labels), the different tests on the predictive variables that this tree must perform, called "nodes". When all the nodes have been crossed, we arrive at a final decision (the attribution of the label "POS" or "NEG" in our case) called a "sheet".

The test to be performed for a fixed node is identified according to the criterion used for the tree. For a classification tree this criterion can be Shannon entropy or Gini diversity index. In our modeling, both criteria were tested but it was the Gini index that was retained because it gave the best results. This index is calculated from the distribution of the data and can be calculated for each of the explanatory variables in the dataset (i.e. in this case, the spectrum value for each Raman shift, or the value of each major component if PCA is implemented). For a given node, the closer this index is to 0, the more this node is said to be "pure", i.e., that it puts forward a criterion allowing good discrimination. In addition, by testing all the explanatory variables in each node, we normally find for each step the explanatory variable to give the best discrimination between the remaining explanatory variables in the branch of the current tree. The optimization of a decision tree therefore consists in finding a succession of nodes giving the lowest possible Gini index to allow the best overall classification.

By $X_N$ it is meant the $N^{th}$ Raman shift. This is not the value at N $cm^{-1}$, but the $N^{th}$ value of the data list of a Raman spectrum stored in the unit 3.

Figure 7:
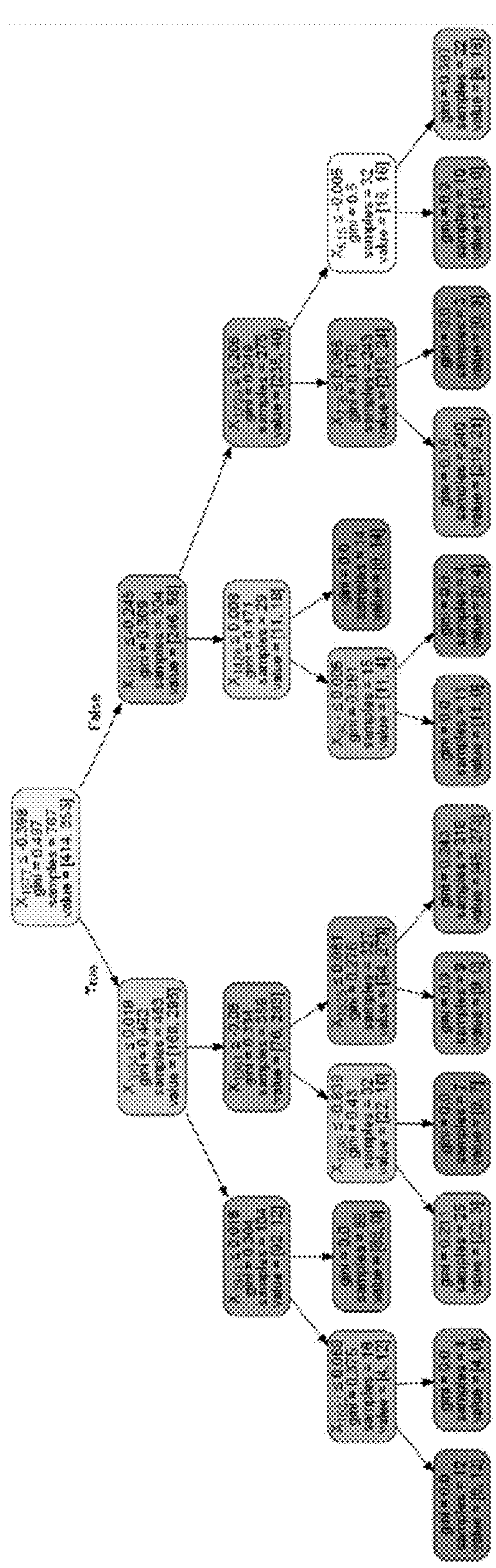
FIG. 7 illustrates an example of a decision tree, deliberately left small, for the classification of spectra used in the context of the present invention FIG. 8 schematically illustrates a neural network used in the context of the present invention

FIG. 7 gives an example of a decision tree, deliberately left small, for the classification of the spectra of our study.

In fact, these types of trees can quickly become very large. For this representation, we set the maximum depth of the tree (which is a hyper-parameter of the model) to 5 so that it remains understandable. For each node, we see which test is done on which variable (e.g. $X_{1877}<-0.398$) as well as the associated Gini index. The "samples" line declares the number of training samples that have arrived at this node and the "value" line gives the number of NEG and POS patients this represents, respectively.

Once these models have been understood, several models can then be considered together. This is called a random forest. We will speak of a random forest of 300 trees when we use 300 different trees for modeling. If these forests have the name "random", it is because each of the trees that constitute it is not trained on the same database, which would eliminate the interest of using different models. Indeed, we make in the original database a random draw of as many datasets as we want to integrate tree in our forest. Thus, we train different predictive models that achieve a majority vote for the final decision. Random forests naturally have more hyper-parameters than decision trees, including the number of trees to use or whether or not you can do bootstrapping.

The random forest used for STRam data classification uses the following hyperparameters:

Bootstrap: Yes

Criterion: Gini

Number of trees: 350

Maximum depth: 11

Maximum number of features: auto

Minimum number of samples in a group for separation: 1

Random state (this is a parameter to which a value is set so that the dataset randomly drawn from the database is reused for each random forest. Any random result will be repeated identically if the Random state is identical): 5000 (The parameter Random state is used for the repeatability of model optimization, it is not a parameter that needs to be optimized)

Neural Network

There are several types of neural networks. Those we have used for the embodiments of the invention described are called Multi-Layer Perceptron (MLP) and are based on the principle of backpropagation of the error.

Figure 8:
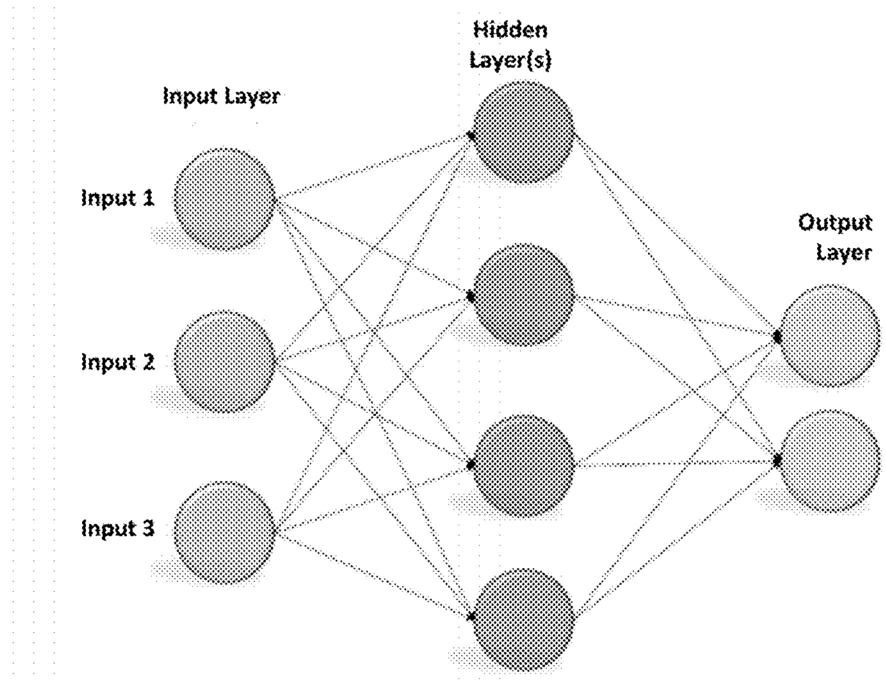
Figure 9:
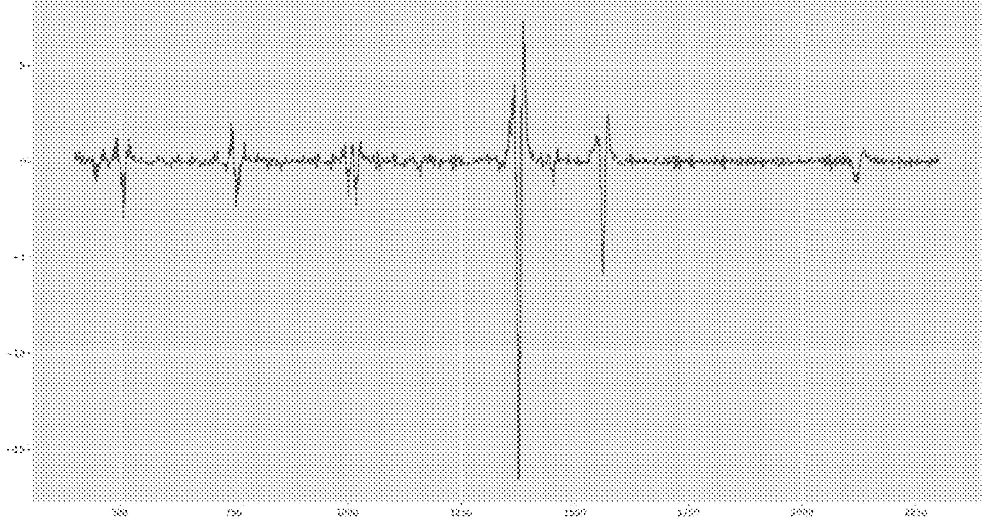
FIG. 9 illustrates the appearance of MIRASA spectra after pre-treatment.

An MLP is a set of elementary units, called neurons, established in different layers. The first layer contains as many neurons as there are explanatory variables in the dataset (here, 1959, or 20 after dimension reduction), and the last contains as many neurons as there are possible labels (here, 2). The number of intermediate layers (also called hidden layers) and the number of neurons in these layers are hyper-parameters of the model. All neurons in one layer are connected to all neurons in the next layer. We classically represent a neural network as illustrated in FIG. 8.

Thus, a neuron can be seen as a mathematical function f, called activation function, of the form:

$$y=f(X_1, \ldots, X_N)$$

In addition, the output of all neurons is weighted by a coefficient, called weight and specific to each connection, which is one of the parameters optimized during training. There are several methods to optimize weights called "solver" or "solution provider". The most common are gradient descent methods but the choice of this method is also a hyper-parameter of the model.

The function f is of the same type for all neurons of the different hidden layers and represents one of the hyper-parameters of the model. This function is different for the input layer and the output layer and also represents, in each of these two cases, a hyper-parameter of the model.

Finally, the "alpha" parameters (penalty term) and the learning rate, classically known by the neural network specialist, are hyper-parameters relating to how the error committed by the model must impact the optimization of the different weights of the network during the backpropagation of the error.

The MLP optimized for the classification of MIRASA data resulting from the optimization phase using GridSearchCV uses the following hyper-parameters:

Activation function: Sigmoid

Alpha: $10^{-5}$

Number of hidden layers: 1

Number of neurons in the hidden layer: 100

Initial learning rate: $10^{-2}$

Learning rate: constant

Solver: stochastic descent of the gradient

Random state: 5000

Pretreatment

In order to select the best spectral pretreatments for modeling, it has been developed within the framework of the present invention a wide variety of pretreatments for use on spectra of surface enhanced Raman spectroscopy (SERS) data. These optional pre-treatments include:

Average reduction, and/or

SNV, and/or

Normalization by the maximum, and/or

Standardization by extrema, and/or

Smoothing by Savitzky-Golay algorithm, and/or

Derivation of order 1 and 2 by Savitzky-Golay algorithm, and/or

Baseline reduction.

These pretreatments can be combined, for example a baseline reduction can be performed and then a derivation of the spectra. However, some pre-treatments are not worth combining. For example, the use of an SNV implies achieving an average reduction. Combining these two pre-treatments is therefore not of interest. In this sense, the software medium of the unit 3 takes as input an integer N and generates, from the pretreatments present in the database, all the "coherent" series of N possible pretreatments, i.e., the series not comprising two (or more) pretreatments which carry out similar operations, or the series not comprising two pretreatments for which the implementation of one is detrimental to the implementation of the other. Once this list of pretreatments is generated, we can then train as many models and compare their performance Model performance was measured by validation, meaning that the database data was broken down into a training set, representing 80% of the initial positive and negative data, and a validation set, containing the remaining 20%. Once again, it is important to ensure that the spectra from the same patient are all in the same training or validation group.

The validation method is different from the test method. A test consists of training a model and testing its performance on an independent dataset. Here, although we can a priori assume that the validation set is independent, we train several models and we keep the one giving the best results on this validation set.

After studying the various pre-processing generated by the software medium of the unit 3, it was obtained that the best pre-processing for MIRASA data was smoothing, baseline correction followed by order 2 derivation. The appearance of MIRASA spectra after pre-treatment is given in FIG. 9.

Figure 10:
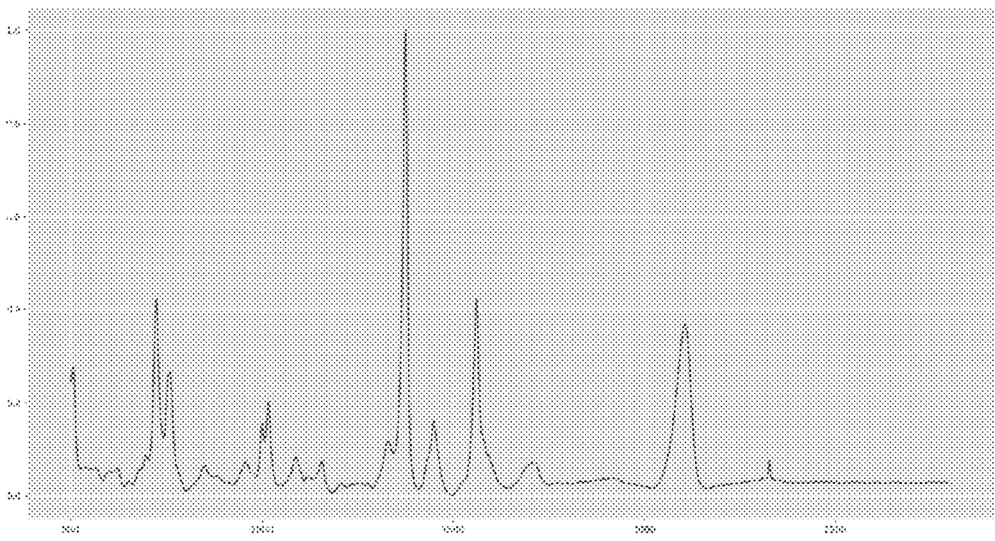
FIG. 10 shows the appearance of STRam spectra after complete pretreatment

For STRam spectra, as described above, a saturation phenomenon is observed for some patients at the beginning of the range. These saturations leading to unwanted variability in the data, it was chosen to remove the part of the spectral range before 500 $cm^{-1}$. After this choice, the best pre-processing obtained using the software medium of the unit 3 for STRam data corresponds to smoothing, baseline correction and normalization by extrema. FIG. 10 shows the appearance of STRam spectra after complete pretreatment.

Prediction

The STRam spectra are first preprocessed as mentioned above before passing through each of the 350 trees in the random forest. The different nodes minimizing the Gini criterion identified during the training phase are applied to the spectrum and a predicted label is obtained for each tree. There is then a majority vote between 350 predictions and the final label predicted by the STRam model is obtained for the spectrum.

Figure 11:
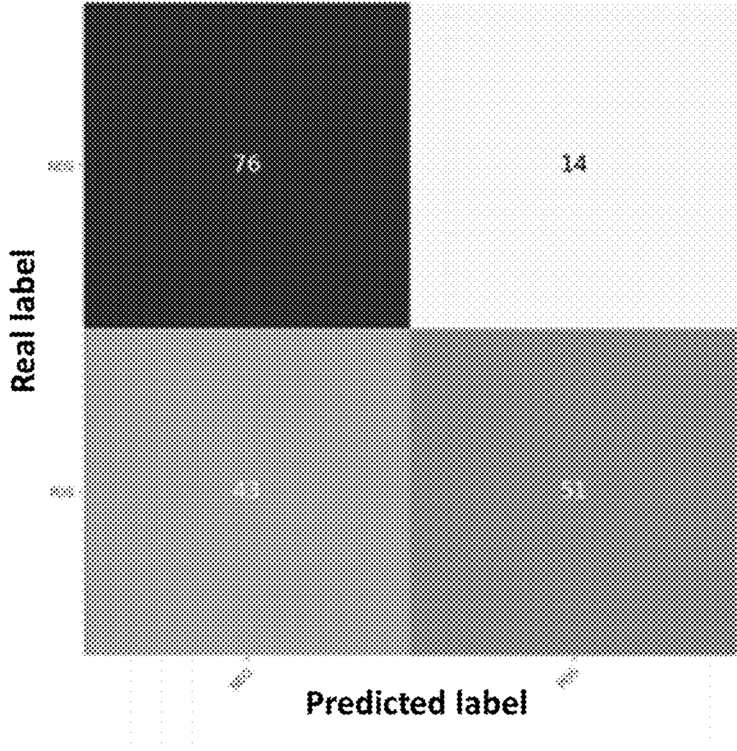
FIG. 11 illustrates the confounding matrix obtained in validation for the STRam model

As mentioned earlier, part of the dataset has been set aside to optimize pre-processing in validation. These are 10 positive patients and 10 negative patients corresponding, for STRam, to a total of 90 spectra labeled NEG and 94 spectra labeled POS. When the model is applied to all of these spectra, without taking into account the belonging of several spectra to the same patient, we obtain the confusion matrix presented in FIG. 11.

Figure 12:
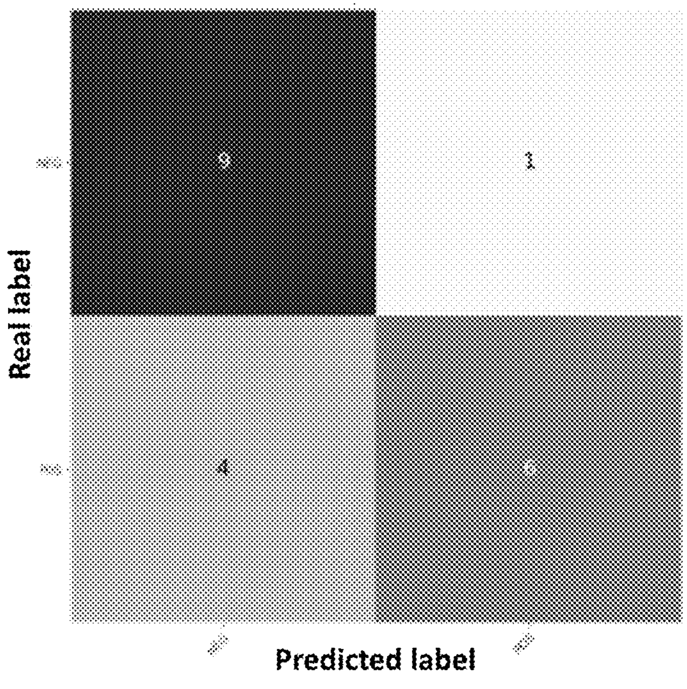
FIG. 12 illustrates the confounding matrix for patient prediction of the STRam model in validation

These results are associated with an overall accuracy of 69%, sensitivity of 54% and specificity of 84%. These values show that it is difficult to correctly identify POS patients. However, we have several spectra (up to 9) per patient. Thus, by performing a majority vote of the predictions made for the same patient, we obtain the confusion matrix of FIG. 12.

The use of several spectra per patient allows to obtain a better prediction since we obtain an overall accuracy of 75%, a sensitivity of 60% and a specificity of 90%.

As for STRam, MIRASA spectra are first preprocessed using the pretreatment identified by the software medium of the unit 3. Here, the model is a multi-layer perceptron. Thus, the data passes successively through the different layers of the neural network before arriving at the output layer. If the final layer of a multi-layer perceptron contains, in classification, as many neurons as classes to predict, it is because each of these neurons is associated with one of the labels present in the training base. The class predicted by an MLP corresponds to the class associated with the neuron with the largest output value.

Figure 13:
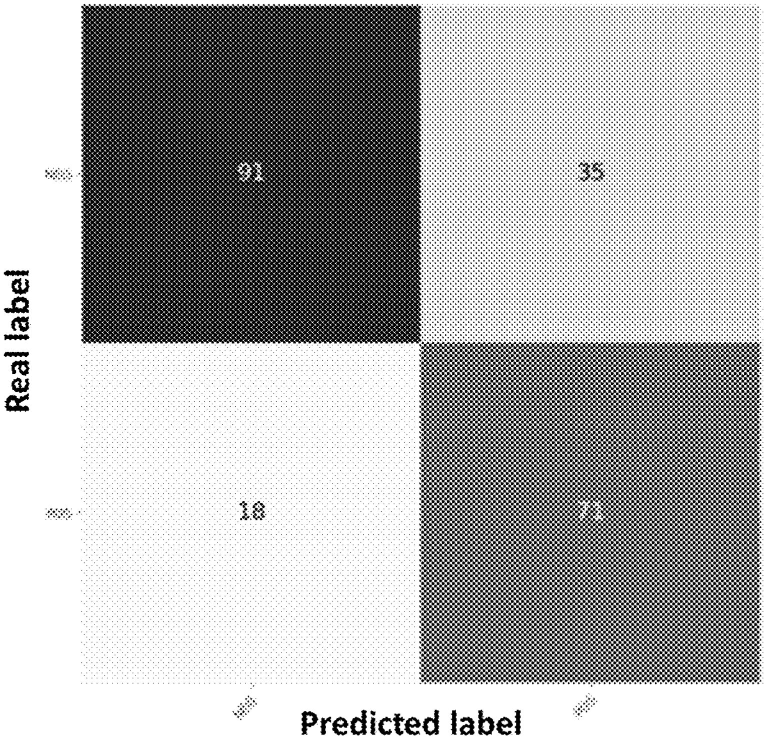
FIG. 13 illustrates the confounding matrix obtained in validation for the MIRASA model

The validation set for MIRASA data consists of 126 NEG labeled spectra as well as 89 POS labeled spectra. Thus, the confusion matrix obtained in validation is given in FIG. 13.

Figure 14:
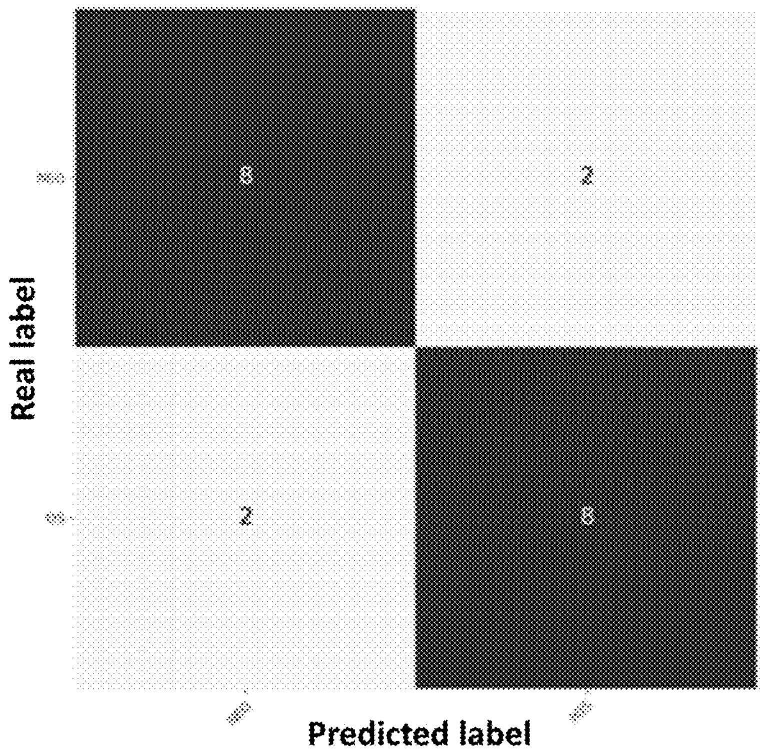
FIG. 14 illustrates the confounding matrix for patient prediction of the MIRASA model in validation

This time, we obtain an overall accuracy of 75% for a sensitivity of 79% and a specificity of 72%. Similar to STRam data, using the fact that each patient is associated with multiple spectra, an overall prediction of the MIRASA model described by the confounding matrix given in FIG. 14 can be obtained.

In this way, an overall accuracy of 80% is obtained, equal to sensitivity and specificity.

As part of the application of these models to the detection of the presence (or not) of the SARS-CoV-2 virus, we were able to observe that the use of several spectra allowed to increase the robustness of the models. For this reason, it was decided that for the final prediction, several spectra would be used. The number of 4 spectra has for the moment been stopped.

In addition, when predicting each spectrum, it is possible, by constructing models, to calculate a percentage of certainty of the model in its prediction. Thus, rather than performing a majority vote of the 4 spectra, which could lead to a tie, it is preferable according to the invention to average the probabilities of belonging to all the spectra of the same patient and then choose the label that corresponds to the maximum probability. This allows the final prediction to be matched with a confidence index equal to the average probability that the model calculates for the predicted label. An answer with a reliability of less than 60% is then derived from spectra for which the predictions were uncertain, allowing the software of the unit 3 to signal that it would be better to repeat this measurement rather than rely on this result. Beyond 60%, there is 2 times more chance that the predicted label is correct rather than false. This 60% barrier is set for the moment but may have to change.

Example 1

Detection of the Presence of SARS-CoV-2

1.1. Material and Method

According to a first example, nasopharyngeal swabs are taken from people.

The samples are processed with lysis buffer and the RNA is isolated by adsorption on a silica matrix and washing.

A solution containing native gold particles with an average diameter of 150 nm at a concentration of 0.15 mg/ml (Metrohm AUNP-COL) is centrifuged at 18,000 g for 1 minute.

30 microliters of the sample containing the purified RNA are put in contact with the nanoparticle pellet and then the whole is stirred to obtain a homogeneous medium.

Deposits of 10 microliters are made on a blade covered with aluminum foil and the spectra are made with an ST-Ram sensor from Metrohm with a power of about 500 mW with a wavelength of 785 nm. It is used between 10 and 100% of its power, preferably between 50 and 100% of its power. The integration time of the measurement is between 15 and 60 seconds.

A second example, the results of which are presented below, is that nasopharyngeal swabs are taken from individuals and unloaded in a transport environment.

A solution containing native gold particles with an average diameter of 100 nm at a concentration of 0.15 mg/mL (AUNP-COL Metrohm) is centrifuged to 800 g for 45 minutes.

20 microliters of the transport medium containing the nasopharyngeal specimen are contacted with 10 μL of the nanoparticle pellet and then the whole is stirred to obtain a homogeneous medium.

Deposits of 10 microliters are made on an aluminum slide and the spectra are made with an STRam sensor from Metrohm with a power of about 500 mW with a wavelength of 785 nm. It is used between 10% and 100% of its power, preferably between 50% and 100% of its power. The integration time of the measurement is between 1 and 30 seconds.

1.2. Results:

The results are presented in FIG. 1.

The method according to the present invention is sensitive since it allows a good classification of patients (see the sensitivity column of the table of FIG. 1) so it gives few false positive patients; It is specific (see the specificity column of the table in FIG. 1) so it allows to distinguish negative patients. It has a very high Youden index. This index is calculated according to the following formula (sensitivity+specificity)−1.

Figure 3:
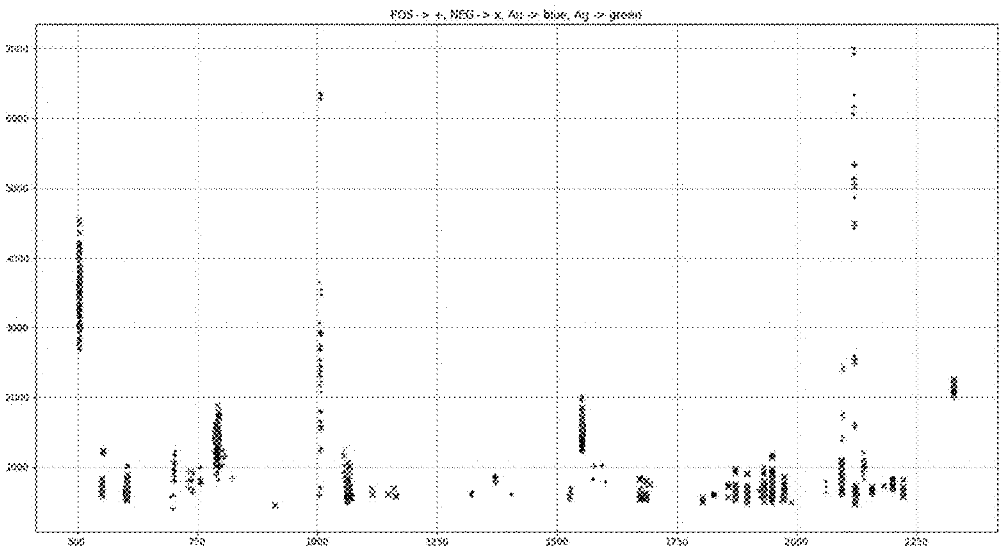
FIG. 3 illustrates the presence of peaks in positive patients (+) and in negative patients (x) when using gold nanoparticles according to the invention

The specific peaks of SARS-CoV-2 are given in FIGS. 2 and 3.

The presence of SARS-CoV-2 in a sample for gold nanoparticles is characterized by the presence of a peak between 560 $cm^{-1}$ and 760 $cm^{-1}$ (typically at 660 or 727 $cm^{-1}$), a peak between 1250 and 1500 $cm^{-1}$ (typically at 1374 $cm^{-1}$) and a peak between 2062 $cm^{-1}$ and 2162 $cm^{-1}$ (typically at 2100 or 2112 $cm^{-1}$). The patient from whom the sample was taken is said to be positive for SARS-CoV-2. On the other hand, in the absence of virus in a sample, only a peak between 1100 and 1250 $cm^{-1}$ is visible. The patient is then declared negative for SARS-CoV-2.

Of course, the invention is not limited to the examples just described and many adjustments can be made to these examples without leaving the scope of the invention.

Of course, the different features, shapes, variants and embodiments of the invention may be associated with each other in various combinations insofar as they are not incompatible or exclusive of each other. In particular all the variants and embodiments described above are combinable with each other.

The invention claimed is:

1. A method for detecting SARS-CoV-2 in at least one surface enhanced Raman spectroscopy (SERS) signal obtained from a sample brought into contact with non-magnetic native metal nanoparticles, the method being implemented by a computer and comprising:

a reception of each surface enhanced Raman spectroscopy (SERS) signal obtained from the sample brought into contact with the non-magnetic native metal nanoparticles;

an implementation of a classification model configured to associate each surface enhanced Raman spectroscopy signal received with at least one class representative of a presence or absence of the pathogen in the sample, wherein the classification model is configured to apply at least one treatment relating to at least three peaks in the surface enhanced Raman spectroscopy signal among:

a peak at a Raman offset between 419 $cm^{-1}$ and 459 $cm^{-1}$, or a peak at a Raman offset between 566 $cm^{-1}$ and 606 $cm^{-1}$, or a peak at a Raman offset between 646 $cm^{-1}$ and 686 $cm^{-1}$, or a peak at a Raman offset between 719 $cm^{-1}$ and 759 $cm^{-1}$, or a peak at a Raman offset between 839 $cm^{-1}$ and 879 $cm^{-1}$, or a peak at a Raman offset between 962 $cm^{-1}$ and 1002 $cm^{-1}$, or a peak at a Raman offset between 1006 $cm^{-1}$ and 1046 $cm^{-1}$, or a peak at a Raman offset between 1121 $cm^{-1}$ and 1161 $cm^{-1}$, or a peak at a Raman offset between 1190 $cm^{-1}$ and 1230 $cm^{-1}$, or a peak at a Raman offset between 1339 $cm^{-1}$ and 1379 $cm^{-1}$, or a peak at a Raman offset between 1529 $cm^{-1}$ and 1569 $cm^{-1}$, or a peak at a Raman offset between 1591 $cm^{-1}$ and 1631 $cm^{-1}$, or a peak at a Raman offset between 1662 $cm^{-1}$ and 1702 $cm^{-1}$, or a peak at a Raman offset between 1722 $cm^{-1}$ and 1762 $cm^{-1}$, or a peak at a Raman offset between 1796 $cm^{-1}$ and 1836 $cm^{-1}$, or a peak at a Raman offset between 2058 $cm^{-1}$ and 2098 $cm^{-1}$, or a peak at a Raman offset between 2110 $cm^{-1}$ and 2150 $cm^{-1}$, or a peak at a Raman offset between 2322 $cm^{-1}$ and 2362 $cm^{-1}$, or a peak at a Raman offset between 2460 $cm^{-1}$ and 2500 $cm^{-1}$.

2. The method according to claim 1, wherein the classification model comprises at least one among: a neural network, a random forest, a support vector machine, a relevance vector machine, a PLSDA, and/or a Bayesian model.

3. The method according to claim 1, comprising, between the reception and the implementation of the classification model, a preprocessing step of each surface enhanced Raman spectroscopy signal, the preprocessing step comprising the implementation of at least one of the following pretreatments: a reduction of average, a standard normal variation, normalization by the maximum, normalization by extrema, smoothing by a Savitzky-Golay algorithm, reduction or correction of baseline, a derivation of order 1 or 2.

4. The method according to claim 1, comprising, between the reception and the implementation of the classification model, an automatic choice of the used classification model from several predetermined classification models based on:

a form of sample collection; or a spectrometer model delivering each surface enhanced Raman spectroscopy signal; or data relating to a subject from whom the sample was taken; or a sample transport medium; or the pathogen(s) to be detected.

5. The method according to claim 1, wherein the reception of each surface enhanced Raman spectroscopy signal comprises:

a) the contact between said sample and non-magnetic native metal nanoparticles to obtain a solution or a suspension;

b) the deposit of said solution or suspension on a medium; and c) the detection of each surface enhanced Raman spectroscopy signal emitted by the deposit.

6. The method according to claim 5, wherein the sample is dissolved before contacting a centrifugation pellet comprising said non-magnetic native metal nanoparticles.

7. The method according to claim 1, wherein the non-magnetic native metal nanoparticles have a diameter between 50 and 200 nm.

8. The method according to claim 1, wherein the non-magnetic native metal nanoparticles comprise non-magnetic nanoparticles of a first metal and non-magnetic nanoparticles of a second metal, the nanoparticles of the first metal being different from the nanoparticles of the second metal.

9. The method according to claim 8, wherein the non-magnetic metal nanoparticles of the first metal are gold particles and the non-magnetic metal nanoparticles of the second metal are silver nanoparticles.

10. The method according to claim 1, wherein the reception of each surface enhanced Raman spectroscopy signal comprises:

an excitation light emission of wavelength between 750 and 800 nm, said excitation light reaching the sample, a capture, by a sensor or a spectrometer, of a reflected, transmitted, scattered or backscattered light by the sample while said excitation light reaches the sample.

11. The method according to claim 10, wherein said excitation light reaches the sample, and the spectrometer or sensor implements the capture step while the sample has been brought into contact with the non-magnetic native metal nanoparticles.

12. A kit for detecting the presence of a pathogen in a sample by surface enhanced Raman spectroscopy (SERS), said kit comprising non-magnetic native metal nanoparticles and a software and/or software medium configured to detect the presence of said pathogen in said sample by implementing a method according to claim 1.

13. The kit according to claim 12, wherein the non-magnetic native metal nanoparticles comprise non-magnetic nanoparticles of a first metal and non-magnetic nanoparticles of a second metal, the nanoparticles of the first metal being different from the nanoparticles of the second metal.

14. The kit according to claim 13, wherein the non-magnetic metal nanoparticles of the first metal are gold nanoparticles and the non-magnetic metal nanoparticles of the second metal are silver nanoparticles.

15. The kit according to claim 12, wherein the pathogen detectable is one of the elements of the group comprising viruses, prions, parasites, fungi, yeasts and bacteria and is in particular SARS-CoV-2.

16. The kit according to claim 12, wherein the non-magnetic native metal nanoparticles have an average diameter between 50 and 200 nm.

17. A method detecting the presence of a pathogen in a sample by surface enhanced Raman spectroscopy (SERS), comprising detecting the presence of said pathogen in said sample with the non-magnetic native metal nanoparticles and the software and/or software medium configured to detect the presence of said pathogen in said sample of the kit according to claim 12.

18. The method according to claim 17, wherein said software further provides a diagnosis of the disease related to the presence of said pathogen.

* * * * *